US007566567B2

(12) United States Patent
Liu et al.

(10) Patent No.: US 7,566,567 B2
(45) Date of Patent: Jul. 28, 2009

(54) IMMORTALIZED HEPATOCYTES

(75) Inventors: Jin Liu, Barrington, RI (US); Ronald A. Faris, Providence, RI (US)

(73) Assignee: Multicell Technologies Inc., Woonsocket, RI (US)

( * ) Notice: Subject to any disclaimer, the term of this patent is extended or adjusted under 35 U.S.C. 154(b) by 98 days.

(21) Appl. No.: 10/574,163

(22) PCT Filed: Oct. 7, 2004

(86) PCT No.: PCT/US2004/033091

§ 371 (c)(1),
(2), (4) Date: Mar. 29, 2006

(87) PCT Pub. No.: WO2006/041488

PCT Pub. Date: Apr. 20, 2006

(65) Prior Publication Data

US 2007/0004039 A1 Jan. 4, 2007

Related U.S. Application Data

(60) Provisional application No. 60/510,509, filed on Oct. 10, 2003.

(51) Int. Cl.
*C12N 5/16* (2006.01)
*C12N 5/22* (2006.01)
(52) U.S. Cl. ..................... 435/370; 435/366
(58) Field of Classification Search .................. None
See application file for complete search history.

(56) References Cited

U.S. PATENT DOCUMENTS

| 5,665,589 | A | 9/1997 | Harris et al. |
| 6,046,050 | A | 4/2000 | Strauss et al. |
| 6,107,043 | A | 8/2000 | Jauregui et al. |
| 6,653,105 | B2 | 11/2003 | Triglia et al. |
| 2002/0045262 | A1 | 4/2002 | Prachumsri |

FOREIGN PATENT DOCUMENTS

| EP | 1 083 223 A1 | 3/2001 |
| WO | WO 99/55853 | 11/1999 |
| WO | WO 00/18239 A1 | 4/2000 |

OTHER PUBLICATIONS

G. Luo et al., "CYP3A4 Induction by Drugs: Correlation Between a Pregnane X Receptor Reporter Gene Assay and CYP3A4 Expression . . . ," Drug Metab. Dispos. 30: 795-804 (2002).
A. Madan et al., Effects of Prototypical Microsomal Enzyme Inducers on Cytochrome P450 Expression in Cultured Human Hepatocytes, Drug Metab. Dispos. 31: 421-431 (2003).
G.T. Tucker et al., "Optimizing Drug Development: Strategies to Assess Drug Metabolism/Transporter Interaction Potential—Toward . . . ," Pharmaceutic. Res. 18: 1071-1080 (2001).
T.D. Bjorsson et al., "The Conduct of in Vitro and in Vivo Drug-Drug Interaction Studies: A PhRMA Perspective," J. Clin. Pharmacol. 43: 443-469 (2003).
F. Bost et al., "Inter-Alpha-Trypsin Inhibitor Proteoglycan Family—a Group of Proteins Binding and Stablizing the Extracellular Matrix," Eur. J Biochem. 252: 339-346 (1998).
S. Yang et al., "Administration of Human Inter-•-Inhibitors Maintains Hemodynamic Stability and Improves Survival During Sepsis," Crit. Care Med. 30: 617-22 (2002).
K.E. Thummel & G.R. Wilkinson, "In Vitro and In Vivo Drug Interactions Involving Human CYP 3A," Ann. Rev. Pharmacol. Toxicol. 38: 389-430 (1998).
S. M. Cascio, "Novel Strategies for Immortalization of Human Hepatocytes," Artificial Orgs. 25: 529-538 (2001).
T. Kuroki & N. Huh, "Why Are Human Cells Resistant to Malignant Cell Transformation in Vitro?," Jpn. J. Cancer Res. 84: 1091-1100 (1993).
H. Zur Hausen, "Oncogenic Herpesviruses" in J. Tooze ed., DNA Tumor Viruses ( Rev. Ed. 2, Cold Spring Harbor Laboratory Press, Cold Spring Harbor, N.Y., 1981), pp. 747-798.
M. Popovic et al., "Transformation of Human Umbilical Cord Blood T-Cells by Human T-Cell Leukemia/Lymphoma Virus (HTLV)," Proc. Natl. Acad. Sci. USA 80:5402-5406 (1983).
J.A. Dipaolo et al., "Progressive Changes Induced in Human and Mouse Cells by Human Papillomavirus Type 16 DNA," Cancer Cells 5: 253-257 (1987).
M.K. Patterson, Jr., "Measurement of Growth and Viability of Cells in Culture," Methods Enzymol., 58:141-152 (1979).
L.H. Thompson, "Mutant Isolation," Methods Enzymol. 58: 308-322 (1979).
S. A. Latt et al., "Microfluorometric Detection of Deoxyribonucleic Acid Replication in Human Metaphase Chromosomes," Proc. Natl. Acad. Sci. USA 70:3395 (1973).
S. A. Latt, "Fluorometric Detection of Deoxyribonucleic Acid Synthesis; Possibilities for Interfacing Bromodeoxyuridine Dye . . . ," J. Histochem. Cytochem. 25:913-926 (1977).
P. Perry& S. Wolff, "New Giemsa Method for the Differential Staining of Sister Chromatids," Nature 261:156-158 (1974).
S. Wolff (1981), "Measurement . . . " in E.C. Friedberg & P.C. Hanawalt, eds., DNA Repair: A Laboratory Manual of Research . . . , (Dekker, N.Y., 1981), vol. 1, Park B, pp. 575-586.
E.G. Cormier et al., "CD81 Is an Entry Coreceptor for Hepatitis C Virus," Proc. Natl. Acad. Sci. USA 101:7270-7274 (2004).
J.P. Salier et al., "The Inter-•-Inhibitor Family: From Structure to Regulation," Biochem. J. 351: 1-9 (1996).
G. Grynkiewicz et al, "A New Generation of Ca2+ Indicators with Greatly Improved Fluorescence Properties," J. Biol. Chem. 260:3440-3450 (1985).
E.J. Stanbridge et al, "Human Cell Hybrids: Analysis of Transformation and Tumorigenicity," Science 215:252-259 (1982).

(Continued)

*Primary Examiner*—Vera Afremova
(74) *Attorney, Agent, or Firm*—Jane Babin

(57) ABSTRACT

This invention relates to virally-immortalized hepatocyte cell lines, which are derived from a normal primary human liver cell, have the ability to proliferate in a serum-free media, are nontumorigenic, and produce proteins. These cell lines can be used for toxicity testing of potential therapeutic drugs and chemical entities. The cell lines may also be used for the production of therapeutic plasma proteins.

2 Claims, 13 Drawing Sheets

OTHER PUBLICATIONS

T. Tsurimoto et al., "Stable Expression and Replication of Hepatitis B Virus Genome in an Integrated State in a Human . . . ," Proc.Natl. Acad. Sci. USA 84:444-448 (1987).

C.A. Brenner et al. "Message Amplification Phenotyping (MAP-Ping): A Technique to Simultaneously Measure Multiple mRNAs from Small . . . ," Biotechniques 7: 1096-1103 (1989).

Y.P. Lim et al., "Correlation Between Mortality and the Levels of Inter-alpha Inhibitors in Plasma of Severely Septic Patients," J. Infect. Dis. 188:919-926 (2003).

K. Nawa et al., "Glucocorticoid-Dependent Expression of the Albumin Gene in Adult Rat Hepatocytes," J. Biol. Chem. 261:16883-16888 (1986).

Mills, J.B., et al.; "An HTS Assay for Induction of Enzymes and Transporters Using a Human Hepatocyte Clonal Line and RNA Detection," *Drug. Metlab.* Rev. 34: 124: 2002, Abstract 248.

Czerwinski, M, et al.; "Induction of Major Cytochrome P450 Enzymes in Immortalized Human Hepatocytes," XenoTechniques, vol. 1, No. 1, Oct. 12-16, 2003 ISSX Meeting, Providence, RI (Jul. 19, 2004).

J.H. Lee et al., "Production and Characterization of Immortalized Rat Hepatocytes Secreting Hepatocyte Growth Factor/Scatter Factor," *Hepato-Gastroenterology* 47: 978-983 (2000).

I.J. Schippers et al., "Immortalized Human Hepatocytes as a Tool for the Study of Hepatocytic (De-)Differentiation," *Cell. Biol. Toxicol.* 13: 375-386 (1997).

K. J. Allen et al., "Conditionally Immortalized Mouse Hepatocytes for Use in Liver Gene Therapy," *J. Gastroenterol. Hepatol.* 15: 1325-1332 (2000).

"Immortalized Hepatocytes: A New In Vitro Approach to Enzyme Induction Studies," *Xenotechniques* 1: 1-11 (2003), at http://www.xenotechllc.com/library/downloads/xenotechniquesvol_1_no_1_2003.pdf.

A.M.A. Pfeifer et al., "Simian Virus 40 Large Tumor Antigen-Immortalized Normal Human Liver Epithelial Cells Express Hepatocyte Characteristics and Metabolize Chemical Carcinogens," *Proc. Natl. Acad. Sci. USA* 90: 5123-5127 (1993).

N. Kobayashi et al., "Prevention of Acute Liver Failure in Rats with Reversibly Immortalized Human Hepatocytes," *Science* 287: 1258-1262 (2000).

J.B. Mills et al., "An HTS Assay for Induction of Enzymes and Transporters Using a Human Hepatocyte Clonal Line and RNA Detection," *Drug Metab. Rev.* 34 (Suppl. 2): 124 (2002).

J. Liu et al., "Characterization and Evaluation of Detoxification Functions of a Nontumorigenic Immortalized Porcine Hepatocyte Cell Line (HepLiu)," *Cell Transplant.* 8: 219-232 (1999).

J. Liu et al., "Growth and Metabolic Activity of Activity of Immortalized Porcine Hepatocytes in Extracorporeal Hollow-Fiber Liver Assist Devices," *Artificial Organs* 25: 539-545 (2001).

A.L. Morris et al., "In Vitro Induction of Cytochrome P450S and Drug Transporters Using the Fa2N-4 Immortalized Human Hepatocyte Line," *Drug Metab. Rev.* 35 (Suppl. 2): 125 (2003).

C. Woods et al., "Induction of Genomic Instability in SV40 Transformed Human Cells: Sufficiency of the N-Terminal 147 Amino Acids of Large T Antigen and Role of pRB and p53," *Oncogene* 9: 2943-2950 (1994).

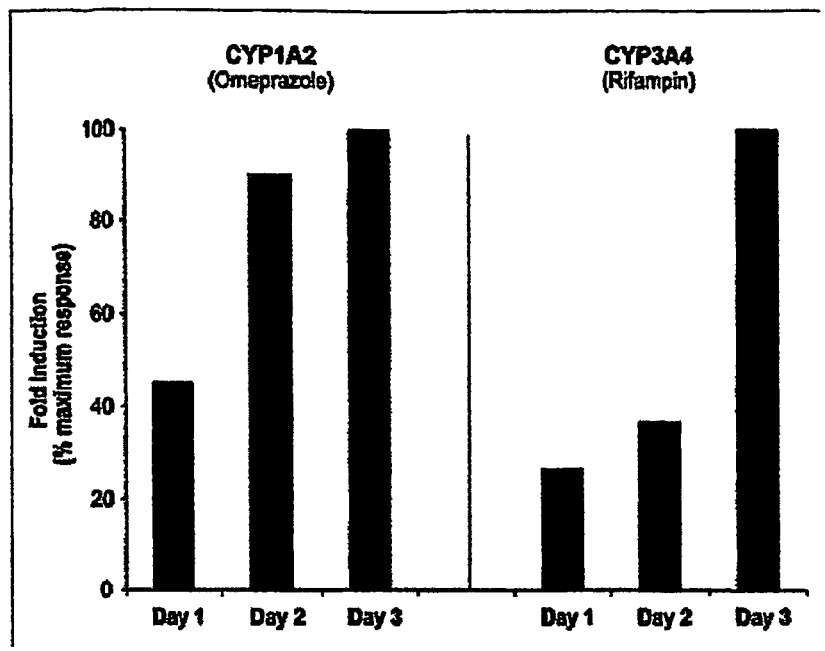
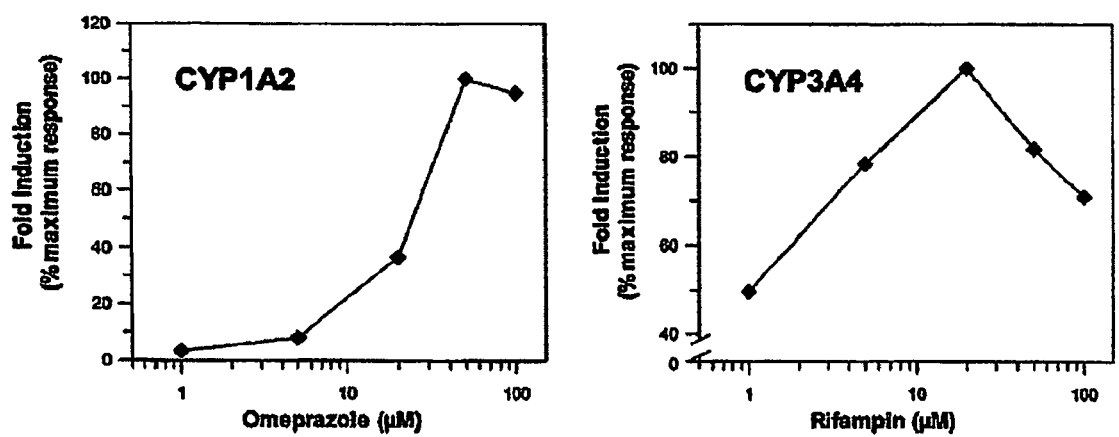

Figure 20
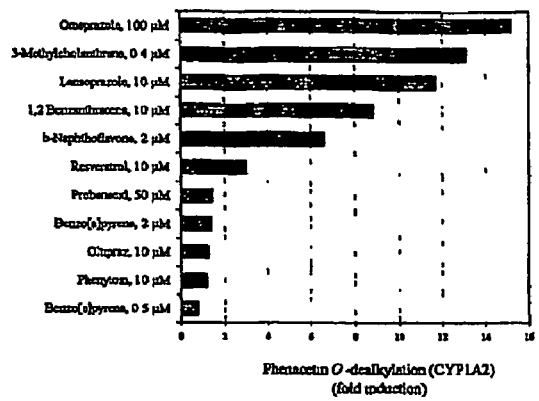
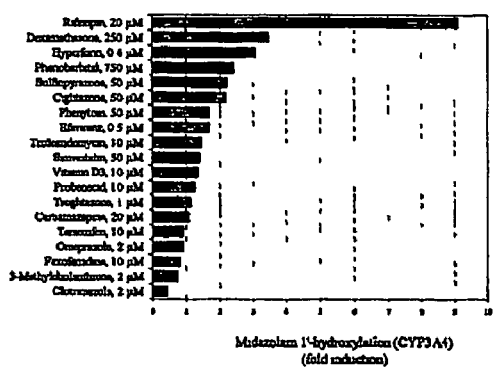
Figure 21
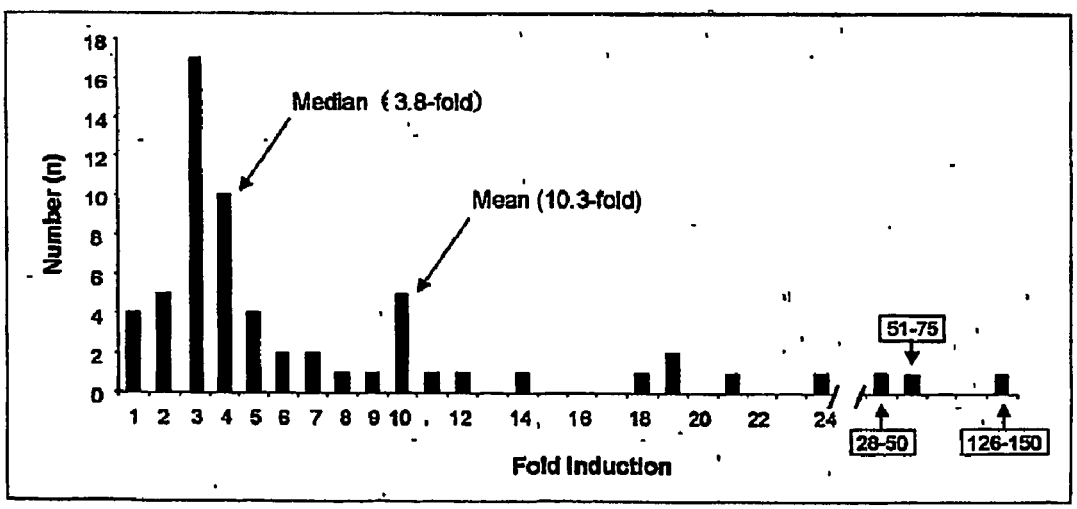

Figure 24
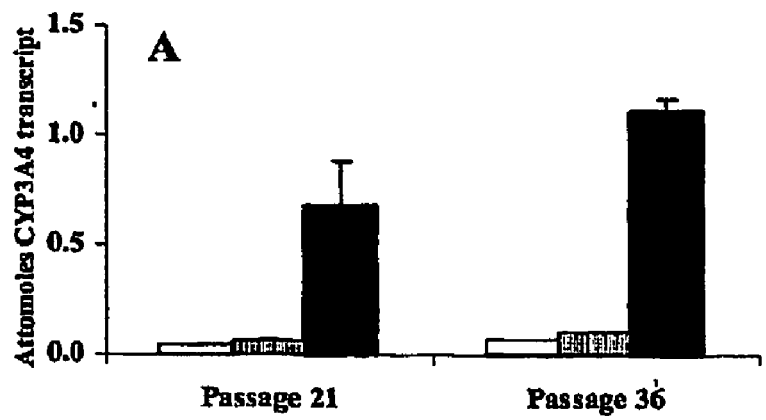
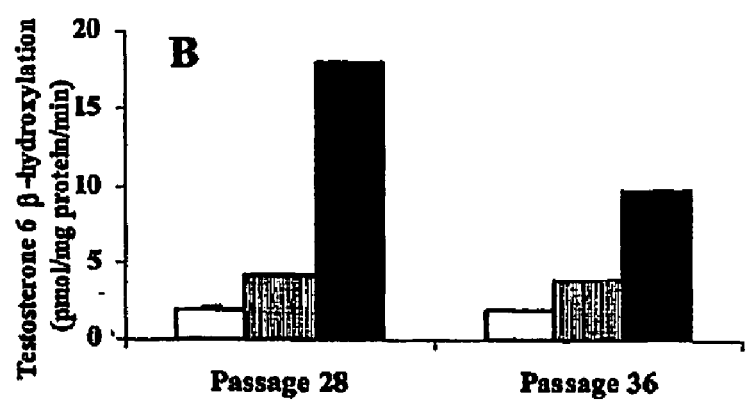
Figure 25
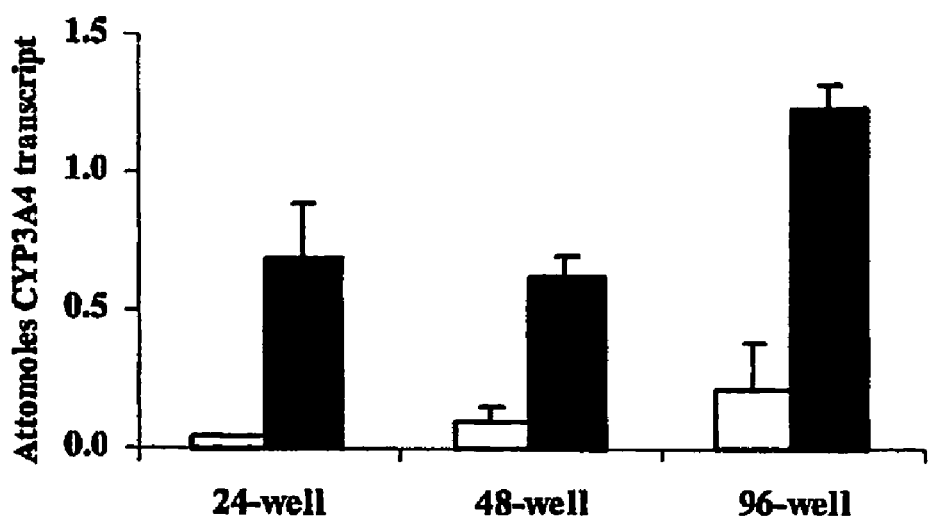

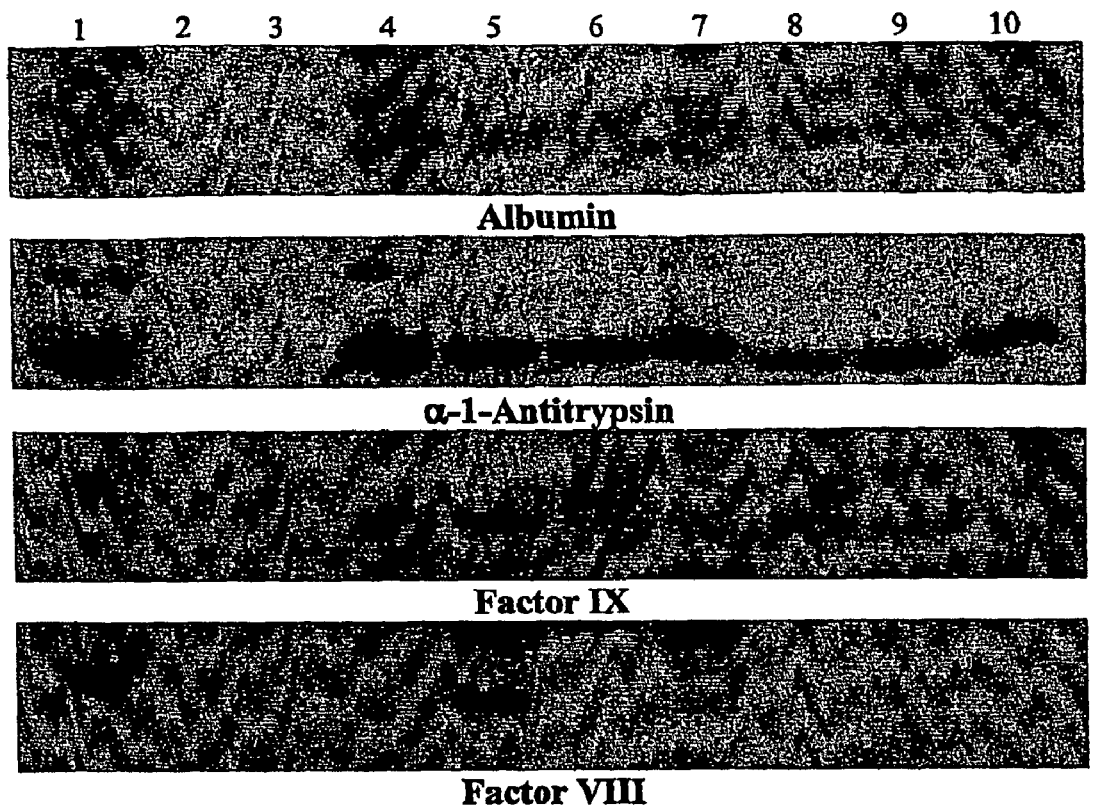
Figure 26
Albumin
α-1-Antitrypsin
Factor IX
Factor VIII
Figure 27
Transferrin

Figure 28
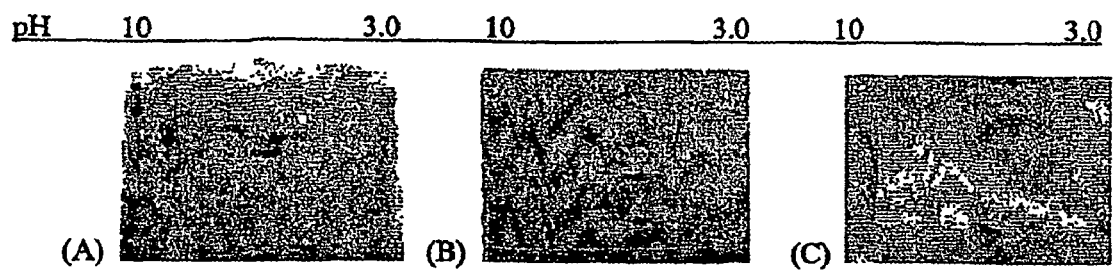
Figure 29
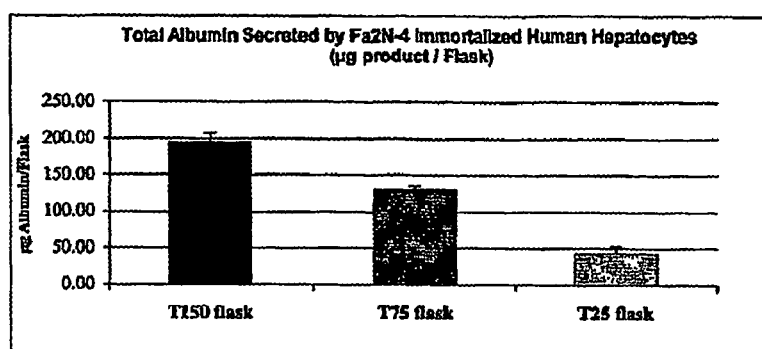
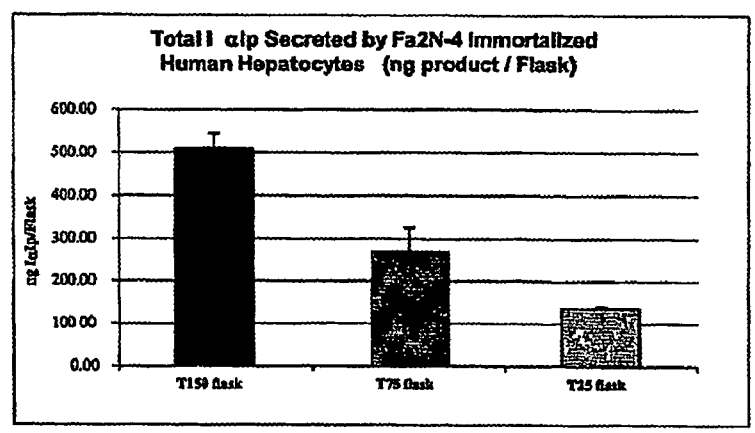
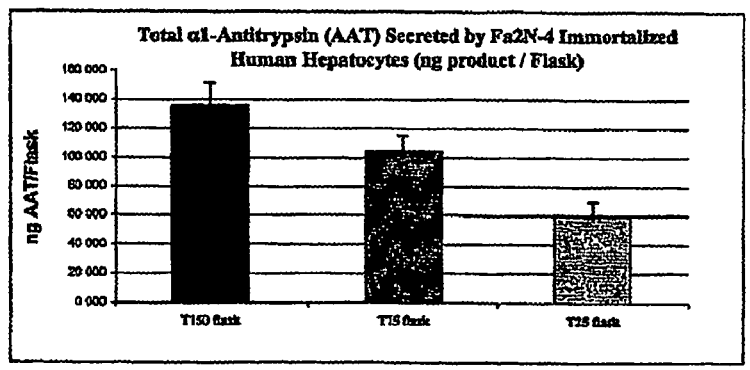

IMMORTALIZED HEPATOCYTES

RELATED APPLICATIONS

This application claims the benefit of U.S. provisional application Ser. No. 60/510,509, filed on Oct. 10, 2003, which is hereby incorporated in its entirety by reference.

GOVERNMENT GRANTS

This invention was made in part with United States government support under grant number 70-NANB7H3070 awarded by Advanced Technology Program of the United States Department of Commerce. The U.S. government has certain rights in this invention.

FIELD OF THE INVENTION

This invention relates to novel nontumorigenic virally-immortalized normal human hepatocyte cell lines and to the use of these cell lines for toxicity and metabolism testing of potential therapeutic drugs and chemical entities, for the replication of viruses and for the production of therapeutic plasma proteins.

BACKGROUND OF THE INVENTION

Toxicity and Metabolism Testing of Potential Therapeutic Drugs and Chemical Entities Drug-induced liver toxicity is an important clinical problem, and several drugs have been withdrawn from the market because of their ability to cause rare but severe (even lethal) cases of hepatotoxicity. Induction of cytochrome P450 (CYP) and related drug-metabolizing enzymes (DMEs), including transporters, is a well-recognized cause of clinically significant drug-drug interactions, as well as a cause of loss of efficacy (pharmacokinetic tolerance) or auto-induction (the process whereby a drug induces its own hepatic metabolism). During drug development, in vitro assays can be used to avoid inducers, and characterize drug-drug interaction potential due to increased drug clearance by the liver. In vitro induction studies traditionally use primary hepatocyte cultures and enzyme activity with selected marker compounds.

CYPs are involved in the metabolism of drugs, primarily in the liver. For example, induction of CYP3A gene expression is caused by a variety of marketed drugs including rifampin, phenobarbital, clotrimazole, and dexamethasone and represents the basis for a number of common drug-drug interactions (Meunier et al., *Expression and induction of CYP1A1/1A2, CYP2A6 and CYP3A4 in primary cultures of human hepatocytes: a 10-year follow-up*, Xenobiotica 30(6): 589-607, 2000; Sahi et al., *Effect of troglitazone on cytochrome P450 enzymes in primary cultures of human and rat hepatocytes*, Xenobiotica 30(3): 273-284, 2000; Luo et al., *CYP3A4 induction by drugs: correlation between a pregnane X receptor reporter gene assay and CYP3A4 expression in human hepatocytes*, Drug Metab. Dispos. 30(7): 795-804, 2002; Madan et al., *Effects of prototypical microsomal enzyme inducers on cytochrome P450 expression in cultured human hepatocytes*, Drug Metab. Dispos. 31(4): 421-431, 2003).

Guidelines for assessing enzyme induction in vitro have been outlined in Tucker et al. (*Optimizing drug development: Strategies to assess drug metabolism/transporter interaction potential—toward a consensus*, Pharmaceutic. Res. 18: 1071-1080, 2001) and Bjorsson et al. (*The conduct of in vitro and in vivo drug-drug interaction studies: A PhRMA perspective*, J. Clin. Pharmacol. 43: 443-469, 2003). These two "consensus reports" identify primary cultures of human hepatocytes as the method of choice—the gold standard—for assessing the enzyme-inducing potential of chemical entities and drug candidates. This in vitro approach, based on a human-derived test system, is superior to an in vivo approach based on tests in laboratory animals because drugs are known to cause enzyme induction in a species-specific manner. For example, the two prototypical inducers, namely omeprazole and rifampin, are efficacious inducers of human CYP1A2 and CYP3A4 and yet they do not induce the corresponding enzymes in rats or mice.

Human hepatocytes play several key roles in preclinical drug development. They can be used to assess the effects of drug candidates on the liver in a clinically meaningful manner (e.g., the induction and cellular toxicity) and, conversely, they can be used to assess the effects of the liver on chemical entities (e.g., drug metabolism and species comparisons). Primary cultures of human hepatocytes have the distinct advantage of exhibiting species-specific induction of CYP isoforms; however, the utility of cryopreserved or plated primary human hepatocytes is restricted by the limited and erratic supply of human liver and by significant inter-individual differences in the expression of DMEs and responses to toxicants.

Cell lines of tumorigenic origin, such as HepG2 and H4IIE, are routinely used for comparison of the in vitro toxicity of candidate compounds. Such cells are unlikely to retain many or most of the factors that predict cell-specific toxicity in vivo. For instance, most tumor-derived cells are not highly differentiated; they rapidly proliferate in culture, which requires enormous energy (ATP consumption) and which may increase their sensitivity to cellular insult compared to non-proliferative cells.

Thus, there is a need for a nontumorigenic immortalized human hepatocyte cell line that retains the properties of a normal human hepatocyte, namely metabolic and transporter function, while offering the distinct advantages of reproducibility and unlimited availability.

Therapeutic Plasma Proteins

There is a great demand for therapeutic plasma proteins (TPPs), such as albumin, $\alpha$-1 antitrypsin (AAT), blood clotting factors VIII and IX, and inter-$\alpha$-inhibitor proteins (I$\alpha$Ip). The production of TPPs by cell-based systems would avoid the hazards of blood-derived products, such as potential contamination with viruses or other pathogens.

Currently, the majority of proteins that have been approved for clinical and therapeutic use are mass-produced by recombinant protein technology. Although these products have been proven safe and effective, not all behave identically to their native counterparts. For example, recombinant factors (rF) VIII and IX are more rapidly cleared following infusion than their plasma derived counterparts. Shapiro, A., E. Berntorp, and M. Morfini, *Incremental recovery assessment and effects of weight and age in previously untreated patients treated with recombinant factor IX*. Blood, 2000. 96 (suppl 1): p. 265a. Recent findings suggest that this is the result of incomplete or inappropriate post-translational modification.

Hemophilia A (Factor VIII deficiency) occurs in 1 in 5,000 to 10,000 males in the United States. In contrast, the incidence of hemophilia B (Factor IX deficiency) is 0.25 in 10,000 males. Currently, plasma-derived and recombinant Factor VIII and IX concentrates are used for the lifetime treatment of hemophilia. It is estimated that three-quarters of the worldwide hemophilia population receive little or no treatment due to a shortage of these TPPs. Thus, there is a clear need for fully functional, fully native blood-clotting factors that overcome the shortcomings of recombinant or blood-derived TPPs.

α-1-antitrypsin (AAT) is a human blood protein. Severe AAT deficiency (hereditary emphysema) is thought to affect around 150,000-200,000 individuals in Europe and the United States. Many respiratory diseases including AAT congenital deficiency, cystic fibrosis and chronic obstructive pulmonary disease are characterized by an imbalance of AAT and elastase in the lung. Administration of supplemental AAT is clinically effective at alleviating the deleterious effects to the lung that occur in these diseases.

Currently, there is only one plasma-derived AAT licensed in the United States, which has been in very limited supply. Thus, there is a clear need for a fully functional, fully native AAT that can overcome the shortcomings of recombinant or blood-derived TPPs.

Sepsis, a disease characterized by an overwhelming systemic response to infection, can strike anyone and can be triggered by events such as pneumonia, trauma, surgery and burns, or by conditions such as cancer or AIDS. In the United States, sepsis is the leading cause of death in the noncardiac intensive care unit and the 11$^{th}$ leading cause of death overall. Currently, treatment for sepsis is limited to attempts to manage the underlying infection and supportive therapy if the infection leads to organ dysfunction. Despite intensive medical care, up to 50% of patients still die from this illness.

Inter-α-inhibitor proteins (IαIp) are natural serine protease inhibitors found in relatively high concentration in plasma that play roles in inflammation, wound healing and cancer metastasis. Bost, F., M. Diarra-Mehrpour, and J. P. Martin, *Inter-alpha-trypsin inhibitor proteoglycan family—a group of proteins binding and stabilizing the extracellular matrix*. Eur J Biochem, 1998. 252: p. 339-346. IαIp is believed to have a predictive value in septic patients. Lim, Y. P., et al., *Inter-trypsin inhibitor: decreased plasma levels in septic patients and its beneficial effects in an experimental sepsis model*. Shock, 2000. 13 (Suppl.): p. 161. In-vivo animal studies using a sepsis rat model have shown that administration of IαIp dramatically improved survival rates. Yang S, et al., *Administration of human inter-alpha-inhibitors maintains hemodynamic stability and improves survival during sepsis*. Crit Care Med. March 2002; 30(3):617-22. The results strongly support the therapeutic potential of IαIp in the management of severe sepsis. Yet, there is no ready supply of IαIp for administration to septic patients. Thus, there is a clear need for fully functional, fully native IαIp to overcome the shortcomings of recombinant or blood-derived TPPs.

There are a number of patents and publications that describe immortalized cell lines: U.S. Pat. No. 6,107,043 (Jauregui); U.S. Pat. No. 5,665,589 (Harris); U.S. Patent App. No. 2002/0045262 A1 (Prachumsri);.and International publication No. WO 99/55853 (Namba). However, to date, among other things, the prior art cell lines do not provide a means to safely, effectively, and cost efficiently perform the protein post-translational modifications, such as glycosylation, that are critical in the production of functional therapeutic plasma proteins; produce simultaneously multiple therapeutic plasma proteins, especially factor VIII protein or factor IX; and maintain the continuous expression of active levels of cytochrome P450 enzyme in a serum-free media. Thus there is a need for a nontumorigenic immortalized human hepatocyte cell line that retains the properties of a normal human hepatocyte, and can be used to produce properly processed therapeutic plasma proteins.

SUMMARY OF THE INVENTION

The present invention relates to nontumorigenic, virally-immortalized human hepatocyte cell lines, that can be maintained in serum-free media, and produce endogenous plasma proteins, such as albumin, α-1 antitrypsin, blood clotting factors VIII and IX, and inter-α-inhibitor proteins (IαIp). In a preferred embodiment, the nontumorigenic, immortalized cell lines comprise the Fa2N-4 (ATCC Accession Number 5566) and Ea1C-35 (ATCC Accession Number 5565) cell lines deposited under the terms of the Budapest Treaty at the American Type Culture Collection (ATCC), Manassas, Va., on Oct. 6, 2003.

In a preferred embodiment of the present invention, the cell lines are derived from normal hepatocytes. Preferably, the cell lines are derived from normal human hepatocytes. More preferably, the cell lines are derived from cryopreserved normal human primary hepatocytes.

In another preferred embodiment of the present invention, the cell lines proliferate easily in media. Preferably, the cell lines proliferate easily in a serum-free media. More preferably, the cell lines proliferate easily in MFE media (MultiCell Technologies Inc., Providence, R.I., USA; XenoTech, LLC, Lenexa, Kans., USA).

In another preferred embodiment of the present invention, the cell lines contain a substantially pure SV40 DNA. Preferably, the SV40 DNA encodes the wild type SV40 large T and small t antigens (TAg). More preferably, the DNA encodes the wild type TAg and does not encode other SV40 gene products.

In another preferred embodiment of the present invention, the cell lines retain their hepatic functions in a serum-free media. Preferably, hepatic functions are the ability to continue to express enzymatic activity and produce proteins. More preferably, hepatic functions include the ability to continue to maintain cytochrome P450 (CYP) enzymatic activities and produce fully-functional therapeutic plasma proteins (TPPs) in a serum-free media.

In another preferred embodiment of the present invention, the cell lines can be used to assess the effects of drug candidates on the liver. Preferably, the cell lines will be used to assess enzyme induction and cellular toxicity.

In another preferred embodiment of the present invention, the cell lines can be used to assess the effects, of the liver on chemical entities. Preferably, the cell lines will be used to assess drug metabolism and species comparisons.

In another preferred embodiment of the present invention, the cell lines continue to produce proteins. Preferably, the cell lines continue to naturally produce plasma proteins. More preferably, the cell lines continue to naturally produce TPPs comprising albumin, α-1-antitrypsin, blood clotting factors VIII and IX, transferrin and inter-α-inhibitor proteins (IαIp).

In another preferred embodiment of the present invention, production of TPPs by the cell lines is measured. Preferably, production of TPPs by the cell lines is measured by detecting their presence in the serum-free media. More preferably, production of TPPs by the cell lines is measured at the protein level rather than at the mRNA level.

In another preferred embodiment of the present invention, the cell lines produce TPPs in serum-free media. Preferably, the cell lines simultaneously produce TPPs out of the same fraction in serum-free media. More preferably, the cell lines simultaneously produce TPPs out of the same fraction in serum-free media without the reoccurring risk of viral contamination.

BRIEF DESCRIPTION OF THE DRAWINGS

FIG. 18 shows a time course of CYP1A2 and CYP3A4 induction in Fa2N-4 cells.

FIG. 19 shows concentration-response curves for CYP1A2 and CYP3A4 induction in Fa2N-4 cells.

FIG. 20 shows the effect of various enzyme inducers on CYP1A2 and CYP3A4 activity in Fa2N-4 cells.

FIG. 21 shows the range of CYP3A4 induction in primary cultures of human hepatocytes. Note the difference between the median and mean induction value.

FIG. 24 shows induction of CYP3A4 in different passages of Fa2N-4 cells. Various passages of Fa2N-4 cells were plated in 24-well plates and exposed to 0.1% DMSO vehicle (open bars), 50 μM dexamethasone (striped bars), and 10 μM rifampin (black bars). (A) The levels of CYP3A4 transcripts were quantified from isolated total RNA. Plot represents the mean±SD from the data of quadruplicate samples. (B) CYP3A4 activity was measured by formation of the testosterone metabolite 6-beta-hydroxytestosterone. Plot represents the mean of duplicate samples. All compounds showed statistically significant increase in transcript versus vehicle control treatment (Student's t-Test, $p<0.05$).

FIG. 25 shows the comparison of CYP3A4 induction in various multiwell plate formats. Induction of CYP3A4 transcript in Fa2N-4 cells after 48 hour exposure to 10 μM rifampin (closed bars) in comparison with vehicle (open bars). Data is from studies conducted in each multiwell plate format as indicated. Plot represents the mean±SD from the data of quadruplicate samples. All compounds showed statistically significant increase in transcript versus vehicle control treatment (Student's t-Test, $p<0.05$).

FIG. 26 shows the following lanes: 1) Human Plasma; 2) Protein Marker Line; 3) Culture Medium (Control); 4) Primary human hepatocytes (72 hr culture); 5) Ea1C-35 monolayer, 72 hrs culture; 6) Ea1C-35, roller bottle, 7-day culture; 7) Ea1C-35 roller bottle/14-day culture; 8) Fa2N-4 monolayer/72 hrs culture; 9) Fa2N-4 roller bottle/7-day culture; 10) Fa2N-4, roller bottle/14-day culture.

FIG. 27 shows an immunoblot using an anti-transferrin antibody with the following lanes: 1) Marker; 2) Ea1C-35p15; 3) Ea1C-35p24; 4) Ea1C-35p29; 5) Ea1C-35 p43; 6) Fa2N-4p10; 7) Fa2N-4-p23; 8) Fa2N-4p31; 9) Fa2N-4p39; 10) Human Plasma.

FIG. 28 shows two-dimensional gel analysis of secreted proteins of the Fa2N-4 and Ea1C-35 cell lines and western blot analysis of the Ea1C-35 gel with anti-Factor-IX antibody.

FIG. 29 shows the expression of plasma proteins albumin, IαIp, and AAT in Fa2N-4 cells grown in T25, T75, and T150 flasks.

DETAILED DESCRIPTION OF THE INVENTION

Abbreviations and Terms

Figure 1:
FIGS. 1 through 8 show the RT-PCR products for the expression analysis of several mRNA transcripts in Ea1C-35 and Fa2N-4 cells. The legend for the gel loading order is outlined in Tables 1 and 2 below.
Figure 2:
Figure 3:
Figure 4:
Figure 5:
Figure 6:
Figure 7:
Figure 8:

In accordance with the present invention and as used herein, the following terms and abbreviations are defined with the following meanings, unless explicitly stated otherwise. These explanations are intended to be exemplary only. They are not intended to limit the terms as they are described or referred to throughout the specification. Rather, these explanations are meant to include any additional aspects and/or examples of the terms as described and claimed herein.

The following abbreviations are used herein:
AAT=α-1-antitrypsin
DME=drug metabolizing enzyme
IαIp=inter-alpha-inhibitor proteins
MCT=MultiCell Technologies
MFE=Multi-Functional Enhancing media
RT-PCR=reverse transcription—polymerase chain reaction
SV40=Simian Virus 40
SV40 TAg=Simian Virus 40 T antigen and t antigen
SV40 tAg=Simian Virus 40 t antigen
TPP=therapeutic plasma protein The term "cell line" refers to a population or mixture of cells of common origin growing together after several passages in vitro. By growing together in the same medium and culture conditions, the cells of the cell line share the characteristics of generally similar growth rates, temperature, gas phase, nutritional and surface requirements. The presence of cells in the cell line expressing certain substances, for example albumin, can be ascertained, provided a sufficient proportion, if not all, of the cells in the line produce a measurable quantity of the substance. An enriched cell line is one in which cells having a certain trait, e.g. expressing albumin, are present in greater proportion after one or more subculture steps, than the original cell line.

The term "clonal cells" are those, which are descended from a single cell. As a practical matter, it is difficult to obtain pure cloned cell cultures of mammalian cells. A high degree of cell purity can be obtained by successive rounds of cell enrichment. As used herein, a cell culture in which at least 80% of the cells possess a defined set of traits is termed a cloned cell culture. Preferably, a cell culture in which at least 90% of the cells possess a defined set of traits is termed a cloned cell culture. More preferably, a cell culture in which at least 98% of the cells possess a defined set of traits is termed a cloned cell culture. The Fa2N-4 and Ea1C-35 cell lines claimed in this invention are clonal cell lines.

The term "immortalization" is defined as the acquisition of an indefinite proliferative capacity. Immortalization may be induced in primary cultured cells and finite cell lines by tranfection with telomerase, oncogenes, or the large T antigen of the SV40, or by infection with SV40. Immortalization is not necessarily a malignant transformation, though it may be a component of malignant transformation.

The term "immortalized" refers to the cell line that grows continually without senescence when cultured in vitro in a suitable growth medium.

The term "virally-immortalized" refers to hepatocytes being transfected or infected with all or part of the viral genome of a wild type or mutant virus. Preferably, the virus is a DNA virus. More preferably, the virus is SV40, which binds to p53 and Rb tumor suppressor proteins, leading to inactivation of their tumor suppressor pathways.

The term "substantially pure" refers to a DNA which has been purified from the sequences which flank it in a naturally occurring state, i.e., a DNA fragment which has been removed from the sequences which are normally adjacent to the fragment, e.g., the sequences adjacent to the fragment in the genome in which it naturally occurs, and which has been substantially purified from other components which naturally accompany the DNA, e.g., DNA which has been purified from the proteins which naturally accompany it in the cell.

The term "hepatocytes" refers to liver cells that are capable of considerable regeneration in response to loss of liver mass (e.g., through hepatotoxic processes, disease, or surgery), and constitute about 80% of the cell population of the liver. They are large polygonal cells measuring between 20-30 μm. Hepatocytes have as many as 200-300 peroxisomes per cells, which are involved in the breakdown of hydrogen peroxide, produced in many of the general cytoplasmic metabolic activities. In addition, peroxisomes have specific oxidative functions in gluconeogenesis, metabolism of purines, alcohol and lipids. The smooth endoplasmic reticulum (sER) in hepatocytes contain enzymes involved in degradation and conjugation of toxins and drugs. Under conditions of hepatocyte challenge by drugs, toxins or metabolic stimulants, the sER may become the predominant organelle in the cells. Hepatocytes perform multiple finely-tuned functions which are critical to homeostasis. Of the variety of cell types in the mammalian body, only hepatocytes combine pathways for synthesis and breakdown of carbohydrates, lipids, amino acids, protein, nucleic acids and co-enzymes simultaneously to accomplish a unique biological task.

The term "isolated hepatocyte" refers to a hepatocyte that has been physically separated from other cells to which it is attached in its natural environment.

The term "primary hepatocyte" refers to a hepatocyte that has been recently isolated from intact liver tissue.

The term "normal primary human hepatocyte" refers to a hepatocyte derived from a nondiseased liver and maintained in vitro for a finite period when cultured in a suitable medium.

The term "cryopreserved human hepatocyte" refers to a normal primary human hepatocyte that was cryopreserved prior to being cultured in a suitable medium.

The term "metabolic activity" refers to the sum total of the chemical reactions that proceed in a cell, including catabolism (breaking down) and anabolism (building up). The metabolic activity in a hepatocyte includes, but is not limited to, the ability to process potentially toxic compounds, e.g., a drug or endogenous metabolite, into a less toxic or non-toxic compound.

The term "cytochrome P450 enzyme" or "CYP" refers to a family of heme-based oxidase enzymes found predominantly in the liver. These enzymes form the first line of defense against toxins and they are involved in the metabolism of hydrophobic drugs, carcinogens, and other potentially toxic compounds and metabolites circulating in the blood. They are found tethered to the surface of the endoplasmic reticulum, where they attach a chemical handle onto carbon-rich toxins. Then, other enzymes may further modify the compound, making the entire molecule more water soluble. This allows the toxins to be eliminated by the urinary and digestive systems. The CYP family is divided into subfamilies, which include, but are not limited to, CYP1A, CYP2A, CYP2C, CYP2D, CYP2E, and CYP3A. Within these subfamilies there are numerous human CYP enzymes, often termed "isozymes" or "isoforms." The human CYP3A, CYP2D6, CYP2C, and CYP1A isoforms are known to be important in drug metabolism. See, e.g., Murray, M., 23 Clin. Pharmacokinetics 132-46 (1992). CYP3A4 is by far the major isoform in human liver and the small intestines, comprising 30% and 70% respectively of the total CYP450 protein in those tissues. Based primarily on in vitro studies, it has been estimated that the metabolism of 40% to 50% of all drugs used in humans involve CYP3A4 catalyzed oxidations. See Thummel, K. E. & Wilkinson, G. R., In Vitro and In Vivo Drug Interactions Involving Human CYP 3A, 38 Ann. Rev. Pharmacol. Toxicol., 389-430 (1998).

The term "hepatic function" refers to liver specific biological functions, which include, but are not limited to, (1) gluconeogenesis; (2) glycogen synthesis, storage, and breakdown; (3) synthesis of serum proteins including, but not limited to, albumin, hemopexin, ceruloplasmin, the blood clotting factors (including, but not limited to, Factors V, VII, VIII, IX, X, prothrombin, and fibrinogen), alpha 1-antitrypsin, transferrin, and anti-thrombin III; (4) conjugation of bile acids; (5) conversion of heme to bile pigments; (6) lipoprotein synthesis; (7) vitamin storage and metabolism; (8) cholesterol synthesis; (9) ammonia metabolism, including urea synthesis and glutamine synthesis; (10) amino acid metabolism, including metabolic conversion and re-utilization of aromatic amino acids; and (11) detoxification and drug metabolism.

Immortalized Human Hepatocyte Cell Lines

This invention relates to virally-immortalized hepatocyte cell lines, which may be derived from normal primary human liver cells, have the ability to proliferate in a serum-free media, are nontumorigenic, and are capable of producing endogenous plasma proteins, such as albumin, α-1 antitrypsin, blood clotting factors VIII and IX, transferrin and inter-α-inhibitor proteins (IαIp) but do not express alpha-fetoprotein when measured at the protein level. In a preferred embodiment, the nontumorigenic, immortalized cell lines comprise the Fa2N-4 (ATCC # PTA-5566) and Ea1C-35 (ATCC # PTA-5565) cell lines deposited under the terms of the Budapest Treaty at the American Type Culture Collection, Manassas, Va., on Oct. 6, 2003.

In a preferred embodiment of the present invention, the cell lines are derived from normal hepatocytes. Preferably, the cell lines are derived from normal human hepatocytes. More preferably, the cell lines are derived from cryopreserved normal human primary hepatocytes.

In another preferred embodiment of the present invention, the cell lines proliferate easily in media. Preferably, the cell lines proliferate easily in a serum-free media. More preferably, the cell lines proliferate easily in MFE media (MultiCell Technologies Inc., Providence, R.I., USA; XenoTech, LLC, Lenexa, Kans., USA).

In another preferred embodiment of the present invention, the cell lines contain a substantially pure SV40 DNA. Preferably, the SV40 DNA encodes the wild type SV40 large T and small t antigens (TAg). More preferably, the DNA encodes the wild type TAg and does not encode other SV40 gene products.

The inventors have developed a large number of proprietary immortalized human hepatocyte cell lines. The majority of these cell lines were created using SV40 TAg as the immortalization gene. This strategy was chosen because transfection of human cells with SV40 TAg can result in cell lifespan extension and in nontumorigenic immortalization since the cells are semipermissive to viral infection. Cascio, S., *Novel strategies for immortalization of human hepatocytes*. Artificial Orgs, 2001. 25: p. 529-538.

Often SV40 TAg immortalized cell lines retain varying levels of the differentiated characteristics associated with the primary cell type and do not display tumorigenicity prior to extensive passage in vitro. Kuroki, T. and N. Huh, *Why are human cells resistant to malignant cell transformation in vitro?* Jpn J Cancer Res, 1993. 84: p. 1091-1100.

The normal human liver primary cells can be made to grow continuously by transfecting the cells with the SV40 TAg gene. Transfection or infection can be accomplished by use of a virus or a plasmid containing the SV40 TAg gene, and may lead to transformation of the cell line. Other transformation vectors may also be useful, such as papilloma virus or Epstein Barr virus. The techniques for making continuous human cell lines are described in the following references: Grahm. F. L., Smiley J., Russell, W. C. and Nairn, R. *Characteristics of a human cell line transformed by DNA from human adenovirus type* 5. J. Gen. Virol., 36:59-72 (1977); Zur Hausen, H. *Oncogenic herpes viruses* In: J. Tooze (ed.), DNA tumor viruses, Rev. Ed. 2, pp 747-798. Cold Spring Harbor, N.Y., Cold Spring Harbor Press (1981); Popovic, M., Lange-Wantein, G., Sarin, P. S., Mann, D. and Gallo, R. C. *Transformation of a human umbilical cord blood T-cells by human T-cell leukemia/lymphon virus (HTLV)*, Proc. Natl. Acad. Sci. USA 80:5402-5406 (1983); DiPaolo, J. A. Pirisi, I., Popeseu, N. C., Yasumoto, S., Poniger, J. *Progressive changes induced in human and mouse cells by human Papillomavirus Type*-16 *DNA*, Cancer Cells 5:253-257 (1987).

Digestion of donor, human liver was performed in vitro with pre-perfusion of oxygen-saturated, calcium-free buffer at 37° C. Pre-perfusion continued until the liver was blanched and followed by perfusion with oxygen-saturated, collagenase buffer until the liver was thoroughly digested (approximately 45 minutes).

To harvest cells, the liver was minced into 1 cm$^2$ pieces with the resulting suspension filtered through a #10 wire screen, then filtered again through a 253 μm nylon mesh. The suspension was centrifuged at 20×g for five minutes at 4° C. to sediment intact parenchymal cells. The pellet was resuspended at 4° C. and washed with washing buffer (3×) to remove all collagenase. The cell pellet was resuspended in 150 ml tissue culture media to yield a final volume of 400-500 ml with a density of 3-4×10$^7$ cells/ml. Trypan blue and lactate dehydrogenase viability assessment was performed on aliquots of this suspension.

The freshly isolated human hepatocytes isolated from donor liver as described above were washed with washing buffer three times by centrifuging at 50×g for 5 minutes. The cell pellet was resuspended in chilled freezing medium (serum-free MFE medium: FBS:DMSO (8:1:1) at a final cell density of 5×10$^6$/ml. Aliquots of the cell suspension were transferred to Nunc Cryovials (1.0 ml/1.5 ml cryovial, 4.5 ml/5 ml cryovial). The cells in cryovials were equilibrated at 4° C. for 15-30 minutes, and the cryovials were then placed in a styrofoam container at −80° C. for at least 3 hours. The vials were then plunged in liquid nitrogen for storage.

Cyropreserved human hepatocytes were rapidly thawed in a 42° C. water bath, washed and plated in MCT's proprietary MFE culture medium. Two days later the immortalizing gene was introduced into the cells by lipofection-mediated transfection.

The Ea1C-35 cell line (ATCC # PTA-5565) was derived from transfection with an immortalization vector containing the 2.5 kb early region of the SV40 genome, which encompasses both the large-T and small-t antigens, and whose expression is driven by the SV40 early promoter. This early region was inserted into the Stratagene pBluescript SK vector backbone and was named pBlueTag. Neomycin resistance was conferred on the transfected cells as a selectable marker by co-transfection of a neo plasmid. Clones were initially selected based on their ability to grow in G418 containing media. The Ea1C-35 cell line was established and maintained in CSM medium.

The Fa2N-4 cell line (ATCC # PTA-5566) was immortalized via lipofection-mediated transfection with a single immortalization vector. The early region of the SV40 genome, contained in the pBlueTag vector, was inserted into a backbone based upon the InvivoGen pGT60mcs plasmid and was named pTag-1. The SV40 TAg coding region is under the influence of a hybrid hEF1-HTLV promoter. The vector also encodes a hygromycin resistance gene as a drug selectable marker. Clones were selected based on their ability to grow in hygro containing media. The Fa2N-4 cell line was established and maintained in MFE.

The Fa2N-4 (ATCC # PTA-5566) and Ea1C-35 (ATCC # PTA-5565) cell lines were deposited under the terms of the Budapest Treaty at the American Type Culture Collection, Manassas, Va., on Oct. 6, 2003.

Both the Fa2N-4 (ATCC # PTA-5566) and Ea1C-35 (ATCC # PTA-5565) cell lines have been maintained in culture for up to 18 months through 150 population doublings. Both of these cell lines went through a crisis stage between passages 15-20. The immortalized cell lines that emerged grow and function when maintained in MCT's proprietary MFE media without serum and can be cryopreserved indefinitely without detriment. The cell lines will also grow and function in other serum free media. The Ea1C-35 cell line will also grow and function in media with serum. The cell lines have a doubling time of 72-96 hours. Results from nude mice transplantation studies have indicated that both the Fa2N-4 (ATCC # PTA-5566) and Ea1C-35 (ATCC # PTA-5565) cell lines are non-tumorigenic.

Toxicity and Metabolism Testing of Potential Therapeutic Drugs and Chemical Entities In another preferred embodiment of the present invention, the cell lines retain hepatic function in a serum-free media. Preferably, hepatic function is the ability to continue to express enzymatic activity. More preferably, hepatic function includes the ability to continue to maintain cytochrome P450 (CYP) enzymatic activities and other drug metabolizing enzymes (DMEs) in a serum-free media.

In another preferred embodiment of the present invention, the cell lines can be used to assess the effects of drug candidates on the liver. Preferably, the cell lines will be used to assess enzyme induction and cellular toxicity.

In another preferred embodiment of the present invention, the cell lines can be used to assess the effects of the liver on chemical entities. Preferably, the cell lines will be used to assess drug metabolism and species comparisons.

Fa2N-4 (ATCC # PTA-5566) and Ea1C-35 (ATCC # PTA-5565) cell lines can be used for enzyme induction studies and to examine compounds for their ability to cause cellular toxicity. CYP1A2 and CYP3A4 activity is inducible in both Fa2N-4 and Ea1C-35 cells which distinguishes these cell lines from other hepatic cell lines. CYP1A2, CYP2B6, CYP2C9, and CYP3A4 activity is inducible in Fa2N-4, which distinguishes this cell line from the Ea1C-35 cell line. The immortalized hepatocyte cell lines of this invention express sufficient CYP for enzyme induction to be assessed based on measurements of enzymatic activity, as well as mRNA levels. Furthermore, the cell lines of this present invention have been shown to conjugate acetaminophen with glucuronic acid and/or sulfate. Thus, the cell lines can be used in assessing the metabolic stability of drug candidates.

Fa2N-4 cells in culture are morphologically and functionally similar to primary cultures of human hepatocytes. The response of this cell line to enzyme inducers closely resembles that observed in cultured primary human hepatocytes, which are considered the in vitro system of choice—the gold standard—for assessing the enzyme-inducing potential of drug candidates. Fa2N-4 cells offer a number of advantages over primary human hepatocytes; some of which make Fa2N-4 cells a promising in vitro test system for higher throughput screening of chemical entities.

In contrast to human liver, the supply of which is limited and erratic, Fa2N-4 cells are available in unlimited supply. Since accessibility to fresh human hepatocytes is reliant on availability of a suitable liver tissue donor, it can take a long time to conduct experiments using hepatocytes isolated from three different livers to verify that a certain compound is an inducer. In addition, plating efficiency of fresh hepatocytes is unpredictable, so it is not uncommon to have a suitable donor, but find that the cells are not usable due to poor plating efficiency or substandard cell health.

Fa2N-4 cells can be passaged and used over several passages while retaining the activity of the major DMEs. With fresh human hepatocytes, cells can only be used one time, making it difficult to compare data between studies. Plateable cryopreserved primary human hepatocytes are an improvement by theoretically allowing multiple experiments at different times from a single donor, or potentially the use of multiple donors at one time. However, plateable cryopreserved primary hepatocytes are in limited supply. Both fresh primary hepatocytes and plateable cryopreserved hepatocytes have donor-to-donor variability, based on the influence of genetics, the environment, and co-medications. There are vast differences seen in the DME profile of donors, leading to the current recommendation of obtaining data from three donors before reaching a conclusion for induction potential of a chemical.

Induction of CYP enzyme activity in Fa2N-4 cells is more reproducible than it is in human hepatocytes. Furthermore, CYP induction in Fa2N-4 cells can be measured in a variety of cell culture formats, including 96-well plates, whereas this is not always possible with human hepatocytes. Thus, the immortalized hepatocytes of this present invention, namely the Fa2N-4 cells, can be a suitable substitute for fresh human hepatocytes in induction studies, and provide the additional attribute of being amenable for higher throughput studies. Fa2N-4 cells are superior to previously published immortal cell lines, as they show induction of a varied number of genes. These cells can be used to determine the induction potential of a drug, with findings consistent with monitoring increased enzyme activity in primary human hepatocytes. Higher throughput cell culturing and analysis via mRNA endpoint enables more compounds to be tested and reduces the cost per compound; two favorable traits for drug discovery assays.

The cell lines of the present invention are uniquely suited for many in vitro applications and testings, including, but are not limited to, the following:

(1) Identification of potential chemotherapeutic drugs: These cells are useful for screening chemicals suitable for the treatment of cancer and related diseases, by growing them in vitro in medium containing the chemical to be tested and then, after a suitable period of exposure, determining whether and to what extent cytotoxicity has occurred, e.g. by trypan blue exclusion assay or related assays (Paterson, Methods Enzymol, 58:141 (1979)), or by growth assays such as colony forming efficiency (MacDonald et al, Exp. Cell. Res., 50:417 (1968)), all of which are standard techniques well known in the art.

(2) Identification of new drug targets. Potential new drug targets can be identified by screening biological and chemical agents for their ability to induce or inhibit genes and metabolic pathways. Chemical and biological substances are screened for their ability to induce or inhibit gene expression or metabolic pathways by adding them to the growth medium of these liver cells and then after a suitable period of time, determine whether a complex of changes, including cessation of DNA synthesis, induction or inhibition of gene expression (as measured by RT-PCR analysis or genomic expression profiling) and production of liver specific proteins (as determined by immunochemical techniques) occurs. Identification of the effects of chemical and biological substances on the induction or inhibition of gene expression and metabolic pathways is a way to identify new drug targets for treating diseases such as cancer.

(3) Studies of metabolism of carcinogens and other xenobiotics: Carcinogens and other xenobiotics may be added to the growth medium of these cells and the appearance of metabolic products of these compounds may be monitored by techniques such as thin layer chromatography or high performance liquid chromatography and the like, and the interaction of the compounds and/or their metabolites with DNA is determined.

(4) Studies of DNA mutagenesis: Substances known or suspected to be mutagens may be added to the growth medium of the cells and then mutations may be assayed, e.g., by detection of the appearance of drug resistant mutant cell colonies (Thompson, Methods Enzymol, 58:308, 1979).

(5) Studies of chromosome damaging agents: Substances known or suspected to cause DNA or chromosomal damage may be added to the culture medium of these cell lines, and then the extent of chromosomal damage may be measured by techniques well known in the art, such as measurement of the frequency of sister chromatic exchange (Latt et al. In: Tice, R. R. and Hollaender, A., Sister Chromatic Exchanges, New York: Plenum Press, pp, 11 ff. (1984)). While there is a wealth of methods for differentiating between sister chromatids, a few simple techniques can suffice for most studies. Representative techniques, employing 33258 Hoechst fluorescence (S. A. Latt et al., Proc. Natl. Acad. Sci. USA 70:3395 (1973); S. A. Latt et al., Cytochem. 25:913 (1977)) or 33258 Hoechst followed sequentially by illumination, SSC incubation, and Giemsa staining (adapted from P. Perry and S. Wolff, Nature 261:156 (1974); S. Wolff (1981), *Measurement of sister chromatid exchange in mammalian cells*. In DNA Repair: A Laboratory Manual of Research Procedures, Vol. 1, Part B (E. C. Friedberg and P. C. Hanawalt, Eds.), Dekker, N.Y.) are just two examples of such techniques that may be used.

(6) Studies of cytotoxicity of drugs, chemical entities, carcinogens, and xenobiotics: Drugs, chemical entities, carcinogens, and xenobiotics may be added to the growth medium of the cells and the viability of the cells as a function of time of exposure may be ascertained using gene expression profiling, dye exclusion, enzyme leakage, colony forming efficiency, etc. assays.

(7) Studies of gene expression: drugs and chemical entities may be added to the culture medium of the cells and changes in gene expression as a function of exposure may be monitored using RNA and protein expression as biological endpoints. Changes may reflect either induction or inhibition of specific genes. For example, cells may be cultured with drugs and chemical entities to identify those agents that modulate the expression of drug metabolism enzymes including but not limited to CYPs designated CYP3A4 or CYP1A2, the multi drug resistance gene, biliary transporters, glucuronyl transferases, glutathione transferases, sulfatases, etc.

(8) The immortalized cells may be used to identify new drugs to treat hepatitis C virus (HCV) infection. The inventors have shown that both the EA1C-35 cell line and the Fa2N-4 cell line express CD81; CD81 is required for HCV mediated viral infection (Cormier, et al, PNAS, 101:7270-7274, 2004). Cell lines can be infected by culturing the cells with HCV positive sera. Cell lines propagating HCV virus may be used to screen for new drugs to treat this chronic infection.

Therapeutic Plasma Proteins (TPPs)

In another preferred embodiment of the present invention, the cell lines continue to produce proteins. Preferably, the cell lines continue to naturally produce plasma proteins. More preferably, the cell lines continue to naturally produce therapeutic plasma proteins (TPPs) comprising albumin, α-1-antitrypsin, blood clotting factors VIII and IX, transferrin and inter-α-inhibitor proteins (IαIp).

In another preferred embodiment of the present invention, production of TPPs by the cell lines is measured. Preferably, production of TPPs by the cell lines is measured by detecting their presence in the serum-free media. More preferably, production of TPPs by the cell lines is measured at the protein level rather than at the mRNA level.

In another preferred embodiment of the present invention, the cell lines produce TPPs in serum-free media. Preferably, the cell lines simultaneously produce TPPs out of the same fraction in serum-free media. More preferably, the cell lines simultaneously produce TPPs out of the same fraction in serum-free media without the reoccurring risk of viral contamination.

Hepatocyte-derived proteins provide a safer, more reproducible approach for producing native plasma proteins for therapeutic applications. This finding is based upon Applicant's data that demonstrates its proprietary, immortalized human hepatocyte cell lines, continue to produce inter-α-inhibitor proteins, a complex family of plasma proteins made by three different polypeptides that are produced from four different genes. Salier, J.-P., et al., *The inter-α-inhibitor family: from structure to regulation*. Biochem J, 1996. 351: p. 1-9.

In contrast to heterologous proteins produced by genetic recombination in mammalian cells, such as Chinese Hamster Ovary cells, TPPs derived from the cell lines of the present invention behave more normally since the secondary post-translational modifications required for complete function was preformed by the native hepatocyte manufacturing process. A significant advantage of using the cells of the present invention to produce TPPs is that the producer cell line is of human origin and therefore leads to a more natural protein. Therefore, since a number of TPPs are synthesized by human hepatocytes, human hepatocyte-based expression systems of the cell lines of the present invention are used to produce TPPs in their "native" form.

Post-translational modifications of TPPs may affect bioactivity, clearance rate in vivo, immunogenicity and/or stability. The immortalized hepatocyte cell lines of the present invention naturally perform the protein modifications, such as glycosylation, that are critical in the production of functional TPPs. The cell lines simultaneously produce multiple TPPs in culture, thus a sequential protein purification scheme will generate multiple products similar to plasma-derived proteins without the reoccurring risk of viral contamination.

TPPs secreted by our hepatocyte-based expression systems of the present invention behave more naturally than recombinant counterparts. For example, the inventors demonstrated that their immortalized human hepatocyte cell lines produce biologically active IαIp and are therefore a strong commercial source for this protein that cannot presently be produced by recombinant technology. Thus, the inventors' production of IαIp in its "native" form leads to a more effective, safe, and cost effective solution to treating life threatening diseases such as sepsis.

The hepatocyte-derived TPPs of the present invention provide a safe, effective, and cost efficient strategy to commercially produce native TPPs, which overcomes the shortcomings of the prior art.

Examples of uses for the cell lines of the present invention as production platforms, include, but are not limited to, the following:

(1) Production of hepatocyte-derived proteins. Cells maintained in suitable medium will naturally express proteins such as blood clotting factors (e.g. factor VIII and Factor IX), albumin, α-1-antitrypsin, transferrin, inter-α-inhibitor proteins, growth factors, etc. that may be purified and used.

(2) Use of recombinant DNA expression vectors to produce proteins of interest. For example, the gene encoding a protein of therapeutic value may be recombined with controlling DNA segments (i.e. containing a promoter with or without an enhancer sequence), transferred into the cell and then the protein produced may be harvested from the culture supernatant or a cellular extract by routine procedures well known in the art.

This may be accomplished by using one or more recombinant vectors that include: (1) the gene encoding the protein to be expressed, a subunit of the protein to be expressed, or a precursor of the protein to be expressed; and (2) at least one control element affecting the transcription of the gene, the control element being operably linked to the gene. The control element is typically a promoter or a promoter-enhancer combination. The characteristics of a suitable vector also include: (1) an origin of replication; (2) restriction endonuclease cleavage sites allowing the insertion of DNA encoding the desired genes; and (3) a selection marker, typically one that confers antibiotic resistance. In one particularly preferred embodiment, the control elements comprise at least one promoter and at least one enhancer.

Suitable recombinant vectors include, but are not limited to, SV40-derived vectors, murine polyoma-derived vectors, BK virus-derived vectors, Epstein-Barr virus-derived vectors, adenovirus-derived vectors, adeno-associated virus-derived vectors, baculovirus-derived vectors, herpesvirus-derived vectors, lentiviral-derived vectors, retrovirus-derived vectors, alphavirus-derived vectors, vaccinia virus-derived vectors, and others. Such vectors typically include a strong and constitutive promoter, at least one intron in the DNA to be expressed, and a polyadenylation signal at the 3'-terminus of the sequence to be transcribed. The addition of a signal peptide to ensure appropriate post-translational modification, such as glycosylation, can be desirable. These vectors and characteristics of vectors are described in S. B. Primrose et al., "Principles of Gene Manipulation" ($6^{th}$ ed., 2001, Blackwell, Oxford, England), pp. 174-201, G. L. Buchschacher, "Lentiviral Vectors" ($1^{st}$ ed, 2003, Landes Bioscience, Georgetown, Tex.) and in T. A. Brown, "Gene Cloning and DNA Analysis: An Introduction" ($4^{th}$ ed., 2001, Blackwell, Oxford, England), all of which are incorporated herein by this reference.

Methods for isolating DNA encoding plasma proteins to be expressed and for inserting such DNA into these vectors are also well known in the art. These methods are described, for example, in S. B. Primrose, "Principles of Gene Manipulation" ($6^{th}$ ed., Blackwell, Oxford, 2001), incorporated herein by this reference. In general, suitable DNA for cloning can be obtained from reverse transcription of specific mRNAs, which can be followed by application of the polymerase chain reaction (PCR) to amplify the DNA; such DNAs are generally known as cDNA. DNA can be inserted into the vectors by techniques that generally involve cleavage of the vectors with specific restriction endonucleases and insertion of the DNA at the cleavage sites.

Methods for transforming or transfecting the virally-immortalized human hepatocytes are well-known in the art and need not be described further in detail here. In general, such methods include, but are not limited to, lipofection, calcium-phosphate-mediated transfection, transfection mediated by DEAE-dextran, transfection by electroporation, transfection by biolistics, and transfection using polybrene. These transfection methods are described in J. Sambrook & D. W. Russell, "Molecular Cloning: A Laboratory Manual (3d ed., Cold Spring Harbor Laboratory Press, Cold Spring Harbor, N.Y., 2001), vol. 3, ch. 16, incorporated herein by this reference.

In many cases, it is desirable to incorporate one or more reporter genes into the vector to assess the efficiency of transfection. The gene of choice is under the control of strong ubiquitous promoter-enhancer combinations. These include those from the immediate early genes of human cytomegalovirus, the Rous sarcoma virus long terminal repeat, or the human β-actin gene. An example of a suitable reporter gene is the chloramphenicol acetyltransferase (CAT) gene found in the *Escherichia coli* transposon. Detection of expression of the reporter gene can be done by a variety of techniques, such as detection of fluorescence or detection of radioactive products. Reporter genes and their assay are further described in M. A. Aitken et al., "Gene Transfer and Expression in Tissue Culture Cells of Higher Eukaryotes," in *Molecular Biomethods Handbook* (R. Rapley & J. M. Walker, ed., Humana Press, Totowa, N.J., 1998), pp. 235-250, incorporated herein by this reference.

Once the protein has been expressed, it is then necessary to isolate the expressed protein. This is typically performed by standard methods for protein purification. These methods include, but are not limited to, precipitation with salts such as ammonium sulfate, ion-exchange chromatography, gel filtration chromatography, reverse phase high pressure liquid chromatography, electrofocusing, chromatofocusing, and/or immunoaffinity chromatography, using any readily ascertainable property, such as protease activity, to detect the protein. Other purification methods are also known in the art. Protein purification methods are described, for example, in R. K. Scopes, "Protein Purification: Principles and Practice" (3d ed., Springer-Verlag, New York, 1994), incorporated herein by this reference.

In some cases, the expressed protein can be secreted from the cell into the surrounding culture medium. The efficiency of this process depends on the pattern of post-transcriptional modification, such as glycosylation, that the protein undergoes. This pattern affects the processing of the protein within the rough endoplasmic reticulum and the Golgi apparatus and its subsequent secretion. This is described in A. J. Dorner & R. J. Kaufman, "Analysis of Synthesis, Processing, and Secretion of Proteins Expressed in Mammalian Cells" in *Gene Expression Technology* (D. V. Goeddel, ed., Academic Press, San Diego, 1991), pp. 577-598, incorporated herein by this reference. The cloning vector can also be chosen so that the protein being expressed is fused to another protein, called a tag, which can be used to facilitate protein purification. Examples of tags include glutathione S-transferase, the MalE maltose-binding protein, and a polyhistidine sequence. The resulting fusion protein can then be cleaved with specific proteolysis to remove the tag and result in purified protein.

Other Uses of the Nontumorigenic Virally-Immortalized Hepatocyte Cell Lines

Other examples of uses for the cell lines of the present invention include, but are not limited to, the following:

(1) Studies of malignant transformation by chemical, physical and viral agents, and transferred genes including oncogenes and high molecular weight genomic DNA from tumors, using standard assays such as anchorage independent growth or tumor formation in athymic nude mice. For example, a cloned viral oncogene k-ras (an oncogene present in many liver cell cancers) can be introduced into the hepatocyte cells using strontium phosphate transfection. The subsequent ability of the newly transfected cells to form tumors in mice as well as grow in an anchorage-independent fashion can be assessed.

(2) Use of cells altered by transfer of oncogenes as in paragraph (1) of this section above to screen for potential chemotherapeutic agents (by the techniques described in paragraph (1) of the "Toxicity and Metabolism Testing of Potential Therapeutic Drugs and Chemical Entities" section above) especially those which may be specific for cells transformed by the activation of particular oncogenes or combination of oncogenes.

(3) Studies of cellular biochemistry, including changes in intracellular pH and calcium levels, as correlated with cell growth and action of exogenous agents including but not limited to those described in paragraphs (1) and (2) of this section above and paragraphs (1) through (5) of the "Toxicity and Metabolism Testing of Potential Therapeutic Drugs and Chemical Entities" section above. To study intracellular pH and calcium levels, cells in suitable culture vessels are exposed to fluorescent indicator dyes and then fluorescence emissions are detected with a fluorescence spectrophotometer (Grynkiewicz et al, J. Biol. Chem., 260: 3440-3450 (1985)).

(4) Studies of cellular responses to growth factors and production of growth factors: Identification and purification of growth factors important for growth and differentiation of human liver hepatocyte cells. These cells are particularly useful for such an application since they grow in serum-free media. Therefore, responses to growth factors can be studied in precisely defined growth medium and any factors produced by the cells may be identified and purified without the complication of the presence of serum.

(5) Studies of intracellular communication e.g., by dye scrape loading assays, to determine whether the cells growing in vitro have the ability to communicate via gap junctions. The cultures may be scraped, e.g., with a scalpel, in the presence of a fluorescent dye in the growth medium. Cells at the edge of the wound are mechanically disrupted and therefore take up dye; whether intercellular communication has occurred may be ascertained by determining whether cells distant from the wound also contain dye.

(6) Characterization of cell surface antigens: The cells are incubated with an antibody against the cell surface antigen of interest, and then reacted with a second antibody, which is conjugated to a fluorescent dye. The cells are then evaluated using a fluorescence activated cell sorter to determine whether they are fluorescent and therefore posses the cell surface antigen.

(7) Cell-cell hybrid studies for identification of tumor suppressor activity (Stranbridge et al, Science, 215:252-259 (1982)). To determine whether these cell lines contain tumor suppressor genes, they are fused to malignant tumor cells. The presence of tumor suppressor genes is indicated by loss of malignancy e.g., as detected by loss of ability to form tumors in athymic nude mice, in the hybrid cells.

(8) Identification of novel genes, including transforming genes in the naturally occurring cancer described in paragraph (1) of this section above, growth factor genes as described in paragraph (4) of this section above, tumor suppressor genes as described in paragraph (7) of this section above, using standard molecular biological techniques (Davis et al, Methods in Molecular Biology, New York: Elsevier (1986)) and techniques such as cDNA subtraction cloning and similar processes.

(9) Growth of replicating hepatitis virus (as e.g., HBV, HCV, non-A non-B, HAV and other livertropic virus, e.g., CMV). Establishment of a clonal cell line of human liver hepatocyte cells containing replicating Hepatitis virus using methods of transfection established for human liver cancer cells lines (Sells, M. A. et al, Proc. Natl. Acad. Sci., 84:444-448). Using human liver hepatocyte lines, which contain HBV, the ability of HBV alone as well as in conjunction with chemical liver carcinogens such as aflatoxin B, can be evaluated for malignant transformation using anchorage independent growth assays as well as growth in athymic nude mice. Cell-cell hybrid techniques similar to those in paragraph (7) of this section above can be used to evaluate possible inactivation of tumor suppressor genes by fusion with malignant cells before and after HBV transfection. The screening kits are easily assembled as other screening kits containing cell lines with other conventional components and labeling instructions for performing the test.

(10) The immortalized cells may be used to identify new drugs to treat hepatitis C virus (HCV) infection. The inventors have shown that both the EA1C-35 cell line and the Fa2N-4 cell line express CD81; CD81 is required for HCV mediated viral infection (Cormier, et al, PNAS, 101:7270-7274, 2004). Cell lines can be infected by culturing the cells with HCV positive sera. Cell lines propagating HCV virus may be used to screen for new drugs to treat this chronic infection.

(11) The immortalized cells may be used as a way of expanding cells for liver transplant and liver function assist devices, both implanted and extracorporeal. Also, these cells can have additional genes transfected/infected into them for organ transplant for therapy of inherited metabolic disorders, especially those diseases associated with hepatic degradation (i.e., certain diseases are due to a deletion or abnormality of a particular gene). This gene could then be transfected into our cells, and the cells then expanded for organ transplant.

(12) Studies of liver parasites: The immortalized hepatic cell lines could prove efficacious for studying the life cycle of parasites that invade hepatocytes, including, but not limited to, amebiasis, malaria, nematodes, and roundworms.

(13) Studies of liver diseases: The immortalized hepatic cell lines could be used to study diseases of the liver, including, but not limited to, infectious liver diseases (such as schistosomiasis, yellow fever, echinococcal cysts, amebiasis, and viral hepatitis); drug induced hepatic disease (such as that from tranquilizers (phenothiazines), antibiotics (isoniazid), and anesthetics (halothane)); fatty liver (such as that from excessive caloric intake usually in the form of ethanol, hepatotoxins ($CCl_4$ and $PO_4$), and systemic metabolic disorders such as uncontrolled diabetes mellitus and toxemia of pregnancy); cirrhosis (such as that from dietary factors (usually alcohol), following massive necrosis from viral hepatitis, associated with pigment deposition, associated with disease of the bile ducts, and other miscellaneous cirrhoses); tumors; and hemochromatosis (a rare disorder of iron metabolism).

EXAMPLES

The following examples are provided by way of describing specific embodiments of the present invention without intending to limit the scope of the invention in any way.

Example 1

Characterization of Immortalized Human Hepatocytes

Over 100 human hepatocyte clonal cell lines were established by transfecting human hepatocytes with the SV40 large T and small t antigen genes under control of the SV40 early promoter. Two cell lines designated Ea1C-35 and Fa2N-4 are described.

Both cell lines were created by lipofection-mediated transfection of primary cryopreserved human hepatocytes with vectors containing the SV40 largeT and small t antigens. The Ea1C-35 cell line was derived from transfection of cryopreserved human hepatocytes with an immortalization vector containing Blue Tag, a recombinant plasmid containing the early region of wild-type SV40. The Blue Tag vector was constructed as follows: PBR/SV (ATCC) was digested with restriction enzymes KpnI and BamHI to release a 2338 bp fragment (the 239-2468 bp fragment was discarded, with the remainder retained; numbering according to Fiers, W et al Science, 273:113-120) containing the SV40 early promoter and the coding regions from small t and large T antigens. This KpnI/BamHI fragment was inserted into the Bluescript SK vector (Stratagene) to produce Blue Tag; a Bluescript based vector that uses the SV40 promoter to drive T antigen expression. This early region was inserted into the Stratagene pBluescript SK vector backbone and was named pBlueTag. Neomycin resistance was conferred on the transfected cells as a selectable marker by co-transfection of a neo plasmid. Clones were initially selected based on their ability to grow in G418 containing media. The Ea1C-35 cell line was established in MCT's proprietary serum containing media, CSM. The Ea1C-35 cell line can be maintained in either CSM or MFE.

The Fa2N-4 cell line was immortalized via lipofection-mediated transfection with a single immortalization vector. The early region of the SV40 genome, contained in the pBlueTag vector, was inserted into a backbone based upon the InvivoGen pGT60mcs plasmid and was named pTag-1. The T-antigen coding region is under the influence of a hybrid hEF1-HTLV promoter. The vector also encodes a hygromycin resistance gene as a drug selectable marker. Clones were selected based on their ability to grow in hygro containing media. The Fa2N-4 cell line was established and maintained in MFE.

Example 2

Expression of Liver Specific Transcription Factors

Since retention of liver specific transcription factors is a prerequisite for expression of hepatic functions, clonal cell lines were initially screened by RT-PCR using primers for human HNF1, HNF3, HNF4α, HNF4γ and C/EBP and albumin. Briefly, total RNA was prepared from $10^6$ cells of each clonal cell line using the micro-isolation method of Brenner et al. (*Message amplification phenotyping (MAPPing): a technique to simultaneously measure multiple mRNAs from small numbers of cells*, Biotechniques 7(10): 1096-1103, 1989). 50 μg of *E. coli* rRNA (Sigma) was used as a carrier to facilitate the isolation of RNA from a small number of cells. RT-PCR reactions were carried out using the Perkin Elmer Cetus, GeneAmp RNA PCR Kit. One μg of total RNA was reverse transcribed using random hexamers and M-MLV reverse transcriptase according to the supplier's instructions. The PCR reaction was carried out using oligonucleotide primers that defined nucleotide fragments unique for each transcription factor. The primers were commercially synthesized and purified by Cruachem (Fisher Scientific). The PCR reaction was carried out for 30 cycles using an annealing temperature of 58° C. for 1 min. The PCR products were visualized in a 1% agarose gel after staining with ethidium bromide. Positive control samples included RT-PCR analysis of total RNA of freshly isolated human hepatocytes (not shown). Both cell lines expressed all five hepatocyte associated transcription factors, as shown below in Table 1. Albumin production was measured as an indicator of hepatocyte specific gene expression. As shown below in Table 1, both cell lines secrete albumin into the serum free conditioned medium as detected by ELISA assay using an antibody that recognizes human albumin.

TABLE 1

| Clones | HNF-1 | HNF-3α | HNF-4α | HNF-4γ | hC/EBP | Albumin (ug/mg protein)[1] |
|---|---|---|---|---|---|---|
| Fa2N-4 | + | + | + | + | + | 2.79 |
| Ea1C-35 | + | + | + | + | + | 0.3 |

Example 3

Reverse-Transcription Polymerase Chain Reaction Analysis for Expression of mRNA Transcripts RT-PCR analysis was performed on two immortalized human hepatocyte cell lines designated Ea1C-35 and Fa2N-4. Cells were plated on type I collagen coated dishes and maintained in MFE medium. Cultured cells were treated with rifampin (10 μM) for 3 days or an equal volume of DMSO (control).

The following primers were used for the RT-PCR analysis: Albumin, Asialoglycoprotein II receptor, HNF-1α, HNF-3, HNF-4α, HNF4γ, c/EBP, UGT 1A1, UGT 2B4, SXR, RXRα, RXRβ, CAR, CYP1A2, CYP2A6, CYP2C9, CYP3A4, CYP2D6, CYP2E1, Cytochrome c, and NADPH.

RT-PCR analysis was performed on two immortalized human hepatocyte cell lines, Ea1C-35 and Fa2N-4, to screen for expression of hepatocyte specific transcription factors (e.g. HNF-1α, HNF-3, HNF-4α, HNF4γ, C/EBP), liver specific genes (e.g. albumin and asialoglycoprotein receptor), transcription factors controlling drug metabolizing genes (e.g. SXR, RXRα, RXRβ, CAR) and phase I and phase II DMEs (e.g. CYP1A2, CYP2A6, CYP2C9, CYP3A4, CYP2D6, CYP2E1, and UGT 1A1, UGT 2B4, respectively).

Analysis was performed with and without exposure to rifampin, a known pharmacological inducer of CYP3A4 expression.

RT-PCR analysis revealed that all transcripts examined were expressed by both cell lines but to various levels, as seen in FIGS. 1 through 8. Rifampin induction increased the expression of CYP3A4 transcripts. The legend for the gel loading order for FIGS. 1 through 8 is outlined in Tables 2 and 3 below.

TABLE 2

Legend for gel loading order for FIGS. 1 through 4

| PCR Product | Gel #1 | Gel #2 | Gel #3 | Gel #4 |
|---|---|---|---|---|
| #1 | 100 bp marker | 5 μl | 5 μl | 5 μl | 5 μl |
| #2 | Ea1C-35 p17, DMSO Ctrl | UGT 1A1 | SXR | HNF-1α | Albumin |
| #3 | Ea1C-35 p17, Rifampin | UGT 1A1 | SXR | HNF-1α | Albumin |
| #4 | Fa2N-4 p34, DMSO Ctrl | UGT 1A1 | SXR | HNF-1α | Albumin |
| #5 | Fa2N-4 p34, Rifampin | UGT 1A1 | SXR | HNF-1α | Albumin |
| #6 | Empty | N/A | N/A | N/A | N/A |
| #7 | Ea1C-35 p17, DMSO Ctrl | UGT 2B4 | RXRα | HNF-3 | ASGPR II |

TABLE 2-continued

Legend for gel loading order for FIGS. 1 through 4

Figure 9A:
FIG. 9a shows immunostaining of the Ea1C-35 immortalized hepatocyte cell line for large T antigen that confirms the integration of SV40DNA into genomic DNA of the immortalized cell.
Figure 9B:
FIG. 9b shows immunostaining of cultured Fa2N-4 cells that demonstrates that the proliferating cells continue to express albumin.
Figure 9C:
FIG. 9c shows the morphology of the immortalized cells with well-defined nucleoli and granulated cytoplasm, which are characteristic features of normal primary hepatocytes.

| | PCR Product | Gel #1 | Gel #2 | Gel #3 | Gel #4 |
|---|---|---|---|---|---|
| #8 | Ea1C-35 p17, Rifampin | UGT 2B4 | RXRα | HNF-3 | ASGPR II |
| #9 | Fa2N-4 p34, DMSO Ctrl | UGT 2B4 | RXRα | HNF-3 | ASGPR II |
| #10 | Fa2N-4 p34, Rifampin | UGT 2B4 | RXRα | HNF-3 | ASGPR II |
| #11 | Empty | N/A | N/A | N/A | N/A | the genome. The resulting clonal cell lines, Fa2N-4 and Ea1C-35 have subsequently been maintained in culture for up to 18 months. Both immortalized lines grow and function when maintained in MFE medium and can be cryopreserved and banked. Indirect immunofluorescent staining using polyvalent antibodies against large T antigen and albumin demonstrated that the cell lines continue to express the nuclear localized immortalizing gene (FIG. 9a) as well as express a hepatocyte specific gene characteristic of differentiated function (FIG. 9b). The morphology of the Ea1C-35 cell line is shown below (FIG. 9c).

TABLE 3

Legend for gel loading order for FIGS. 5 through 8

| | PCR Product | Gel #5 | Gel #6 | Gel #7 | Gel #8 |
|---|---|---|---|---|---|
| #1 | 100 bp marker | 5 µl | 5 µl | 5 µl | 5 µl |
| #2 | Ea1C-35 p17, DMSO Ctrl | CYP 3A4 | CYP 2D6 | GAPDH, RT(+), 60° C. | Kit Ctrl, 61° C. |
| #3 | Ea1C-35 p17, Rifampin | CYP 3A4 | CYP 2D6 | GAPDH, RT(+), 60° C. | Kit Ctrl, 60° C. |
| #4 | Fa2N-4 p34, DMSO Ctrl | CYP 3A4 | CYP 2D6 | GAPDH, RT(+), 60° C. | Kit Ctrl, 59° C. |
| #5 | Fa2N-4 p34, Rifampin | CYP 3A4 | CYP 2D6 | GAPDH, RT(+), 60° C. | Kit Ctrl, 60° C. |
| #6 | Empty | N/A | N/A | N/A | N/A |
| #7 | Ea1C-35 p17, DMSO Ctrl | CYP 2C9 | CYP 2E1 | GAPDH, RT(+), 61° C. | N/A |
| #8 | Ea1C-35 p17, Rifampin | CYP 2C9 | CYP 2E1 | GAPDH, RT(+), 61° C. | N/A |
| #9 | Fa2N-4 p34, DMSO Ctrl | CYP 2C9 | CYP 2E1 | GAPDH, RT(+), 61° C. | N/A |
| #10 | Fa2N-4 p34, Rifampin | CYP 2C9 | CYP 2E1 | GAPDH, RT(+), 61° C. | N/A |
| #11 | Empty | N/A | N/A | N/A | N/A |
| #12 | Ea1C-35 p17, DMSO Ctrl | CYP 1A2 | Cyto c | GAPDH, RT(+), 59° C. | N/A |
| #13 | Ea1C-35 p17, Rifampin | CYP 1A2 | Cyto c | GAPDH, RT(+), 59° C. | N/A |
| #14 | Fa2N-4 p34, DMSO Ctrl | CYP 1A2 | Cyto c | GAPDH, RT(+), 59° C. | N/A |
| #15 | Fa2N-4 p34, Rifampin | CYP 1A2 | Cyto c | GAPDH, RT(+), 59° C. | N/A |
| #16 | Empty | N/A | N/A | N/A | N/A |
| #17 | Ea1C-35 p17, DMSO Ctrl | CYP 2A6 | NADPH | GAPDH, RT(−), 60° C. | N/A |
| #18 | Ea1C-35 p17, Rifampin | CYP 2A6 | NADPH | GAPDH, RT(−), 60° C. | N/A |
| #19 | Fa2N-4 p34, DMSO Ctrl | CYP 2A6 | NADPH | GAPDH, RT(−), 60° C. | N/A |
| #20 | Fa2N-4 p34, Rifampin | CYP 2A6 | NADPH | GAPDH, RT(−), 60° C. | N/A |

TABLE 2-continued

Legend for gel loading order for FIGS. 1 through 4

| | PCR Product | Gel #1 | Gel #2 | Gel #3 | Gel #4 |
|---|---|---|---|---|---|
| #12 | Ea1C-35 p17, DMSO Ctrl | CAR | RXRβ | HNF-4α | GAPDH |
| #13 | Ea1C-35 p17, Rifampin | CAR | RXRβ | HNF-4α | GAPDH |
| #14 | Fa2N-4 p34, DMSO Ctrl | CAR | RXRβ | HNF-4α | GAPDH |
| #15 | Fa2N-4 p34, Rifampin | CAR | RXRβ | HNF-4α | GAPDH |
| #16 | Empty | N/A | N/A | N/A | N/A |
| #17 | Ea1C-35 p17, DMSO Ctrl | c/EBP | GAPDH | HNF-4γ | N/A |
| #18 | Ea1C-35 p17, Rifampin | c/EBP | GAPDH | HNF-4γ | N/A |
| #19 | Fa2N-4 p34, DMSO Ctrl | c/EBP | GAPDH | HNF-4γ | N/A |
| #20 | Fa2N-4 p34, Rifampin | c/EBP | GAPDH | HNF-4γ | kit Ctrl |

Example 4

SV40 Mediated Proliferative Activity

Primary human hepatocytes have limited proliferative activity when cultured. In order to overcome this characteristic, SV40 large T and small t antigens were introduced into Immunostaining of Fa2N-4 cells for albumin expression was performed. Cells were plated on type I collagen and cultured in serum free medium for 72 hr. Albumin was visualized by indirect immunofluorescence with a fluorescene conjugated secondary antibody. As shown in FIG. 9b below virtually all of the cells express Albumin.

Example 5

Drug Metabolism Data

Both cell lines continue to catalyze Phase I (CYP) and Phase II conjugative reactions in monolayer cultures based on the metabolism of model substrates. One of the most important Phase I enzymes is CYP3A4, which is responsible for the metabolism of approximately 50% of all drugs. The expression of CYP3A4 can be modulated by many factors including multiple drug intakes that may induce or inhibit the overall expression of this CYP. Therefore the effective therapeutic dose of a drug is determined in part by CYP3A4 expression.

CYP3A4 modulators can be identified by monitoring the transcriptional responsiveness of the gene and by measuring enzymatic activity towards model substrates (i.e. testosterone). For example, transcriptional responsiveness to prototypical pharmacological CYP3A4 inducers (i.e. rifampin) can be assayed by the RT-PCR using specific primers to detect CYP3A4 cDNA. Rifampin-induced CYP3A4 enzymatic activity can also be measured by the production of the 6β-OH-testosterone metabolite when cells are incubated with testosterone. As shown below in Table 4, the Fa2N-4 cell line is more sensitive to CYP inducers than the Ea1C-35 cell line.

In order to demonstrate that the cell lines continue to express Phase II conjugating enzymes, cells were exposed to acetaminophen for 24 hours and conditioned culture medium was collected and analyzed for the production of acetaminophen glucuronide or acetaminophen sulfate conjugates. The production of the acetaminophen glucuronide and acetaminophen sulfate conjugates was measured by HPLC analysis. The results are shown in Table 4. To determine the effect of passage number, the production of acetaminophen glucuronide and acetaminophen sulfate was measured for Fa2N-4 cells after 11, 14, 27, 32, 40, and 41 passages. For passage 41, ammonia clearance was also measured as an indicator of nitrogen metabolism. The results are shown in Table 5. These results indicate that both DME conjugative pathways are intact and that the Fa2N-4 cells can remove ammonia.

TABLE 4

Characteristics of the Fa2N-4 and Ea1C-35 cell lines.

| Cell line | Rifampin treated CYP3A4 mRNA fold induction)* | Control (ug 6β-OH testosterone/mg protein)** | Rifampin (ug 6β-OH testosterone/mg protein)** | Acetaminophen glucuronide ug/mg protein) | Acetaminophen sulfate ug/mg protein) |
|---|---|---|---|---|---|
| Fa2N-4 (p13) | 15.4 | 5.44 | 15.28 | 20.9 | 16.1 |
| Ea1C-35 (p29) | 2.2 | 4.53 | 9.25 | 15 | 21.5 |

*Cells were exposed to vehicle or rifampin for 72 hours. Data is expressed relative to vehicle treated controls.
**Cells were exposed to vehicle or rifampin for 72 hours and then incubated with testosterone for 24 hours. Production of the 6β-OH-testosterone metabolite was quantitated by HPLC analysis and data is expressed per mg total cell protein.

TABLE 5

Effect of Passage Number for Fa2N-4 Cells on Metabolism of Acetaminophen

| Cells | Passage | Acetaminophen Glucuronide (μg/mg protein) | Acetaminophen Sulfate (μg/mg protein) | Ammonia Clearance (mg $NH_3$/mg protein/24 hr) |
|---|---|---|---|---|
| Fa2N-4 | 11 | 15.18 ± 0.74 | 30.26 ± 0.31 | ND |
| Fa2N-4 | 14 | 16.43 ± 1.26 | 29.87 ± 1.83 | ND |
| Fa2N-4 | 27 | 7.93 ± 2.37 | 27.48 ± 2.2 | ND |
| Fa2N-4 | 32 | 10.42 ± 1.45 | 25.37 ± 0.84 | ND |
| Fa2N-4 | 40 | 12.68 ± 2.76 | 25.25 ± 1.99 | ND |
| Fa2N-4 | 41 | 21.4 ± 4.5 | 36.6 ± 1.2 | 246 ± 5.87 |

ND = Not determined

Example 6

Use of Immortalized Hepatocytes to Identify and Rank CYP Inducers

Two lines of evidence indicate that immortalized human hepatocytes can be employed to identify and rank CYP3A4 inducers based on 'induction potency".

Figure 10:
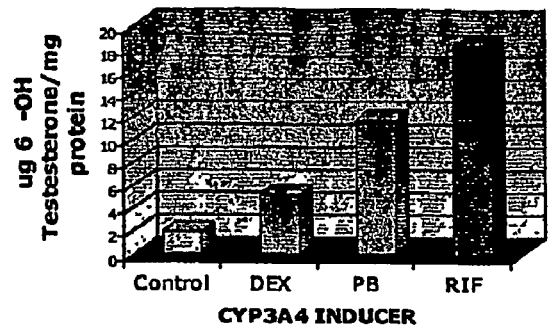
FIG. 10 shows the inducibility of testosterone metabolism after treating Fa2N-4 cells with different CYP3A4 inducers.

First, exposing Fa2N-4 cells to rifampin (10 μM) results in a greater production of the 6-β testosterone metabolite than treating cells with weaker CYP3A4 inducers such as dexamethasone (50 μM) or phenobarbital (1 mM), as shown below in FIG. 10.

Figure 11:
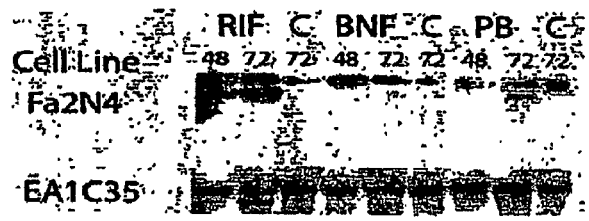
FIG. 11 shows an immunoblot demonstrating the induction of CYP3A4 consequent of treatment of Fa2N-4 and Ea1C-35 with Rifampin (RIF), beta-naphtoflavone (BNF) and phenobarbital (PB). C is the untreated control. It should be noted that the upper band is nonspecific and that BNF, a CYP1A inducer, does not induce CYP3A4 protein expression.

Secondly, immunoblot analysis demonstrated in FIG. 11 that exposure of each of the cell lines to rifampin or phenobarbital for 48-72 hours increased expression of CYP3A4 protein in comparison to vehicle-treated controls; however, exposure to rifampin resulted in a greater increase expression of CYP3A4 protein. The upper band in the immunoblot is nonspecific, and thus BNF, a CYP1A inducer, does not induce CYP3A4 protein expression.

Taken together, these results clearly indicate that the immortalized human hepatocyte cell lines provide an invaluable model to detect constitutive and inducible CYP3A4 expression.

Example 7

Morphological and Functional Similarity to Primary Cultures

Figure 12:
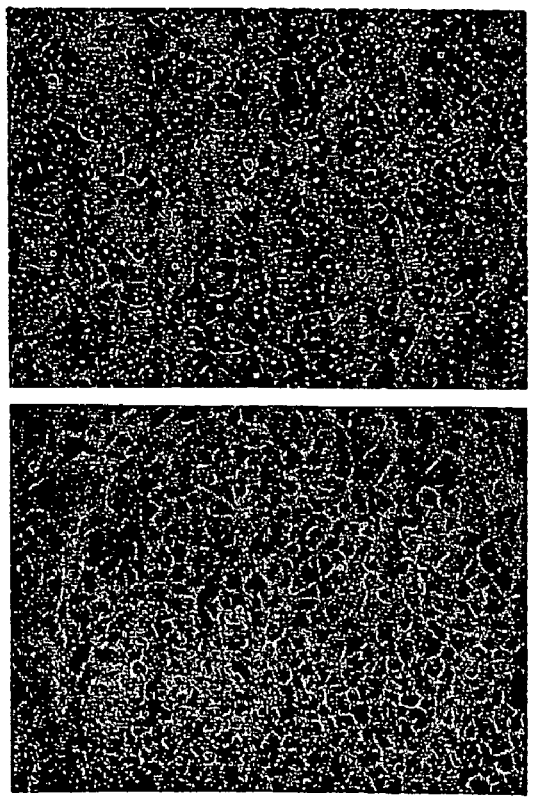
FIG. 12 shows the morphology of human hepatocytes (upper) and Fa2N-4 cells (lower) at the light microscopy level. Note that Fa2N-4 cells look remarkably similar to human hepatocytes.

Cultured Fa2N-4 cells are uniquely similar, both morphologically and functionally, to primary cultures of fresh human hepatocytes. FIG. 12 shows this close morphological resemblance between human hepatocytes (upper panel) and Fa2N-4 cells (lower panel). Numerous CYPs, including CYP1A2, CYP2B6, CYP2C9, and CYP3A4, are inducible in Fa2N-4 cells. The procedure for assessing enzyme induction in Fa2N-4 cells is remarkably similar to that for primary cultures of human hepatocytes.

The Fa2N-4 cells were propagated on a collagen substratum in MFE Support Medium. The cells were detached by trypsinization, isolated by centrifugation, and re-attached to collagen in the desired format (e.g., 6-, 12-, 24-, or 96-well plates). After a two-day adaptation period, the cells were treated once daily for three consecutive days with test article or the appropriate negative and positive controls. Enzyme induction was assessed 24 hours after the last treatment. CYP activity measured in microsomes prepared from the cultured hepatocytes (in vitro activity) was compared with that measured in microsomes prepared directly form human livers (ex vivo activity).

Enzyme induction was assessed in Fa2N-4 cells by incubating the cells with phenacetin (to measure CYP1A2), bupropion (to measure CYP2B6), diclofenac (to measure CYP2C9) or midazolam (to measure CYP3A4). In each case, the final concentration of substrate was 100 μM. Metabolite formation was determined by assaying aliquots of the cell culture medium at various times (up to 8 hours) by LC/MS/MS. To facilitate a comparison of different CYP activities under a variety of conditions, the results were expressed relative to control activity determined at the 8-hour time point.

Figure 13:
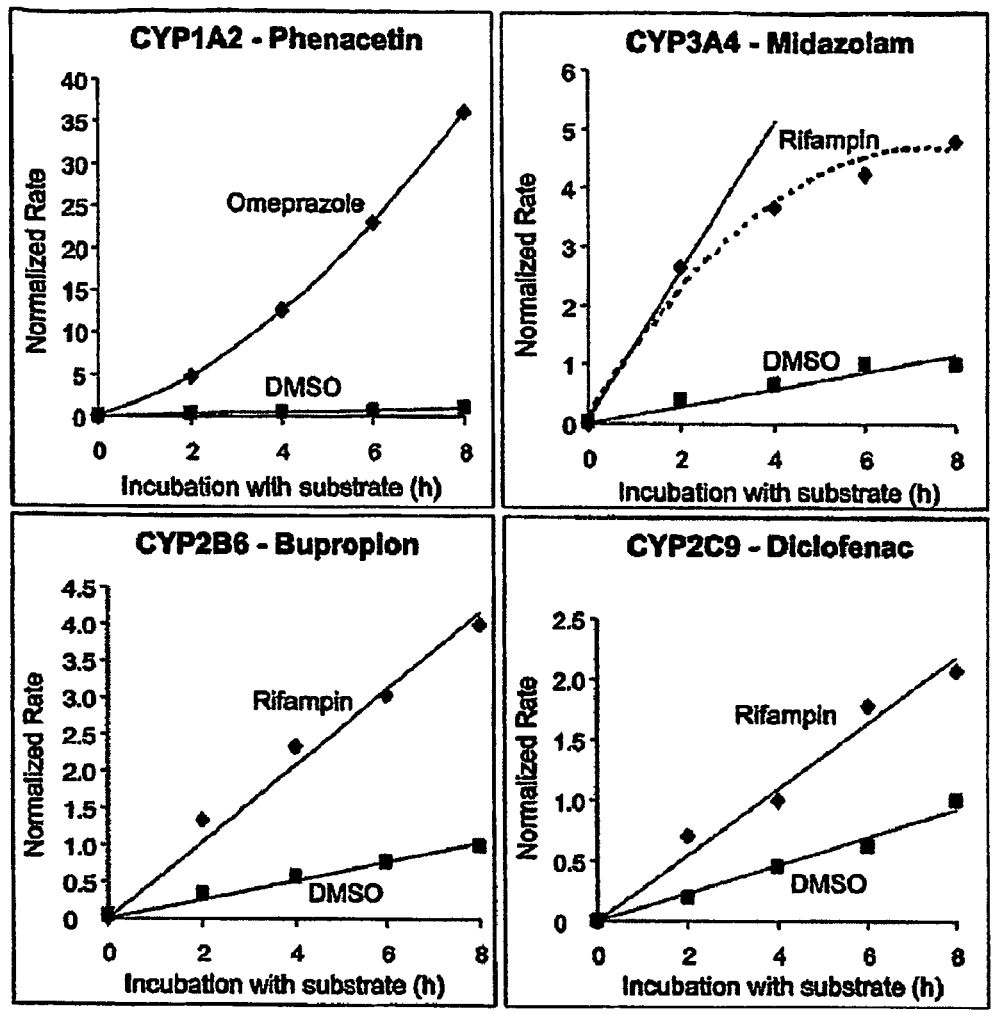
FIG. 13 shows induction of CYP enzymes by omeprazole and rifampin in Fa2N-4 cells, cultured in 6-well plates.

Fa2N-4 cells respond appropriately to enzyme inducers. As in the case of human hepatocytes, CYP1A2 is highly inducible by those agents that activate the Ah receptor, whereas those agents that activate PXR and/or CAR cause induction of CYP3A4 and, to a lesser extent, CYP2B6 and CYP2C9. As shown in FIG. 13, treatment of Fa2N-4 cells (cultured in 6-well plates) with 100 μM omeprazole caused marked induction of CYP1A2 activity, whereas treatment with 20 μM rifampin induces CYP3A4 and, to a lesser extent, CYP2B6 and CYP2C9 activity.

Figure 14:
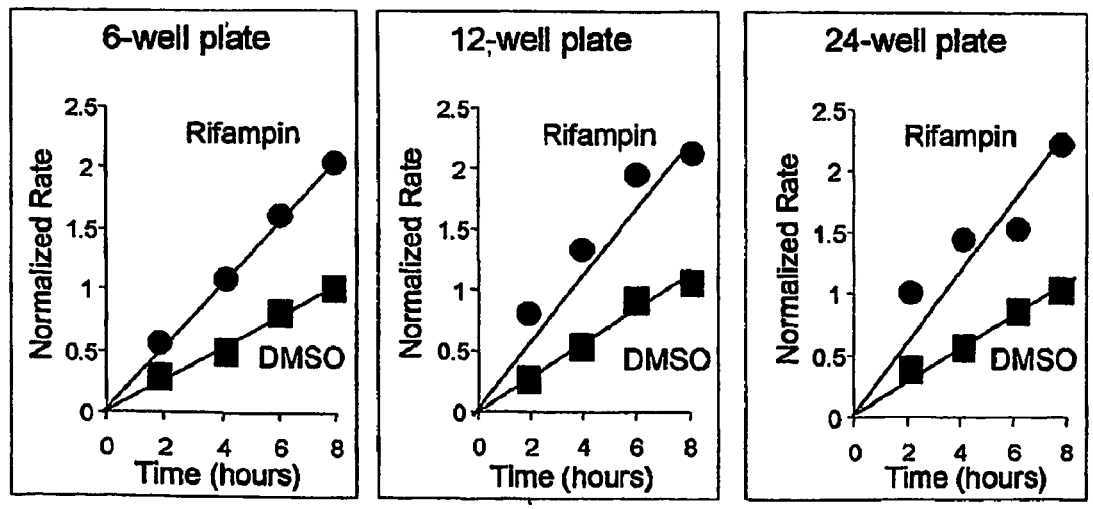
FIG. 14 shows the reproducibility of CYP2B6 induction in rifampin-treated Fa2N-4 cells.
Figure 15:
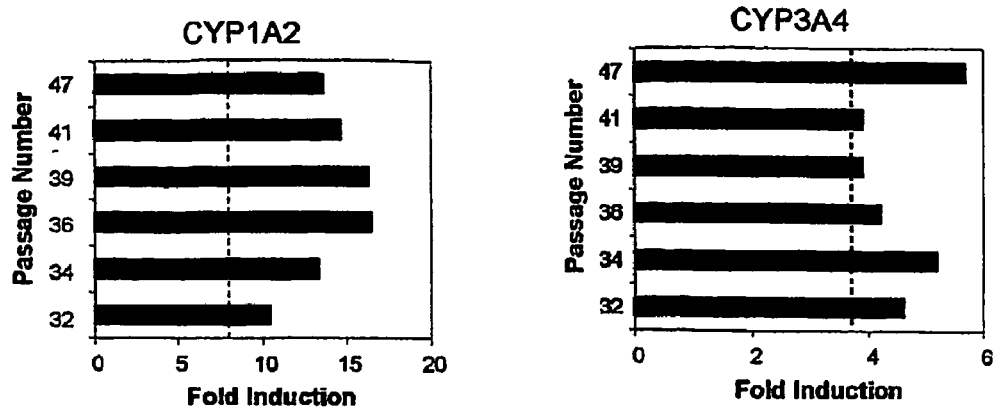
FIG. 15 shows reproducibility of CYP enzyme induction in Fa2N-4 cells across several passages. Dotted lines represent median fold induction in fresh human hepatocytes.
Figure 16:
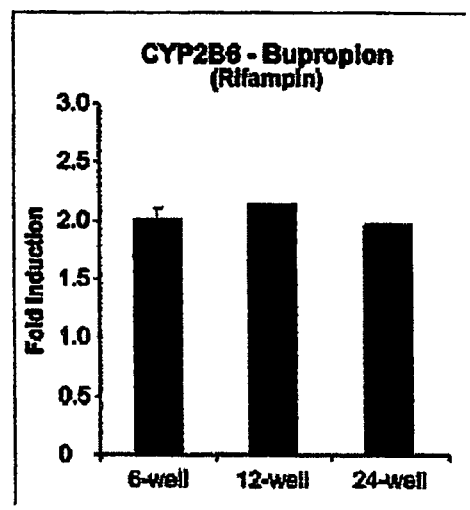
FIG. 16 shows the effect of cell culture format on induction of CYP2B6 in Fa2N-4 cells.

Enzyme induction in Fa2N-4 cells is reproducible from one experiment to the next, and across different sized multi-well plates. FIG. 14 depicts the results of a comparison of the reproducibility of induction of CYP2B6 (bupropion hydroxylase) activity by rifampin, across three different plate formats. Reproducibility of CYP1A2 and CYP3A4 induction across multiple cell passages was also assessed, and those results are shown in FIG. 15. The reproducibility in magnitude of induction across passages 32-47 is excellent for both CYP enzymes, and is superior to the reproducibility of induction typically seen with individual preparations of human hepatocytes. Induction of CYP2B6 in Fa2N-4 cells by rifampin is the same in 6-, 12-, and 24-well plates, as shown in FIG. 16. Identical results were obtained for CYP2C9 (results not shown). These results indicate that differentiated properties of immortalized hepatocytes are highly stable. In terms of reproducibility, the immortalized hepatocyte cell lines of this present invention are superior to primary cultures of human hepatocytes, where the magnitude of CYP induction can vary substantially from one preparation to the next.

Enzyme induction in primary cultures of human hepatocytes is affected by the cell culture format. Thus, as the well size decreases, there is a decline in the magnitude of enzyme induction in primary cultures of human hepatocytes.

Figure 17:
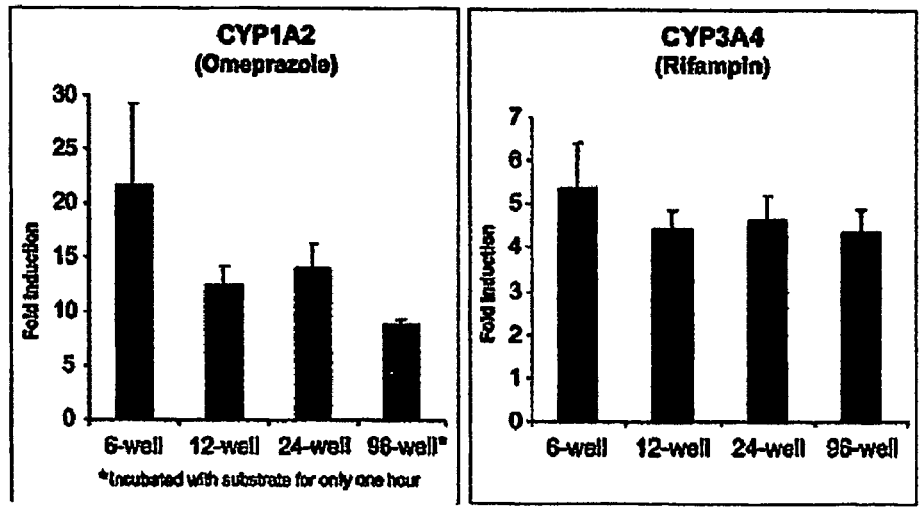
FIG. 17 shows the effect of cell culture format (6-, 12-, 24-, or 96-well plate) on CYP1A2 and CYP3A4 induction in Fa2N-4 cells.

FIG. 17 shows the effect of cell culture format on the induction of CYP1A2 by omeprazole and the induction of CYP3A4 by rifampin. Cell culture format appears to have a slight influence on CYP1A2 induction in that the magnitude of induction was greater in a 6-well than in a 12-, 24-, or 96-well format. However, in all cases, omeprazole induced CYP1A2 activity by at least 9 fold over control. FIG. 17 also shows, that in the case of CYP3A4, induction by rifampin is similar in the 6-, 12-, 24-, and 96-well format. Therefore, cell lines of the present invention provide more reliable enzyme induction across many cell culture formats than do primary cultures of human hepatocytes.

The time course of CYP1A2 and CYP3A4 induction in Fa2N-4 cells are similar to those observed in primary cultures of human hepatocytes. FIG. 18 shows the time course of CYP1A2 and CYP3A4 induction in Fa2N-4 cells.

Enzyme induction in Fa2N-4 cells occurs over an appropriate range of inducer concentrations. The concentration-response curves for CYP1A2 induction by omeprazole and for CYP3A4 induction by rifampin in Fa2N-4 cells are shown in FIG. 19. Similar results are observed in human hepatocytes.

Fa2N-4 cells respond appropriately to those compounds that do and do not induce CYP enzymes in human hepatocytes. For example, as in the case of human hepatocytes, compounds shown previously to activate PXR and induce CYP3A4 in human hepatocytes (Luo et al., *CYP3A4 induction by drugs: Correlation between a pregnane X receptor reporter gene assay and CYP3A4 expression in human hepatocytes*, Drug Metab. Dispos. 30: 795-804, 2002) induce CYP3A4 activity in Fa2N-4 cells, whereas Ah receptor agonists do not, as shown in FIG. 20. Note that clotrimazole is both a CYP3A4 inducer and inhibitor, and thus CYP3A4 induction is masked by its inhibitory effect. Also, as in the case of human hepatocytes, CYP1A2 is highly inducible by those agents that activate the Ah receptor (as shown in FIG. 20).

Table 6 summarizes the magnitude of induction of CYP1A2, CYP2B6, CYP2C9, and CYP3A4 in Fa2N-4 cells and primary cultures of human hepatocytes. In the case of CYP1A2, the magnitude of induction in Fa2N-4 cells was greater than the average fold induction in human hepatocytes. In the case of CYP2B6, CYP2C9 and CYP3A4, the magnitude of induction in Fa2N-4 cells was comparable to the median fold induction in human hepatocytes, but less than the average fold induction. Median induction differs considerably from mean induction in human hepatocytes because the latter is markedly affected by the occasional samples with extremely high values of fold induction. This is illustrated in FIG. 21 for CYP3A4 induction, which ranges from zero (less than 1.5 fold) to 145 fold. Although the mean fold induction of CYP3A4 in human hepatocytes is 10 fold, the median induction, which is a more meaningful comparator, is about 4 fold.

TABLE 6

Comparison of CYP enzyme induction in Fa2N-4 cells and human hepatocytes

| Enzyme (Inducer) | Fa2N-4 Average induction (range) | Human hepatocytes * Average induction (range) | Human hepatocytes * Median induction |
|---|---|---|---|
| CYP1A2 (Omeprazole or BNF) ** | 20 fold (9.3-29) | 13 fold (2-56) | 8.4 fold |
| CYP2B6 (Rifampin) | 2.5 fold (2.0-3.9) | 4.1 or 13 fold *** (up to 14 or 71) | 2.9 or 8.5 fold |
| CYP2C9 (Rifampin) | 2.0 fold (1.6-2.8) | 3.5 fold (1.5-10) | 3.1 fold |
| CYP3A4 (Rifampin) | 5.1 fold (4.0-6.9) | 10 fold (0-145) | 3.8 fold |

* Data from Maden et al., Effects of prototypical microsomal enzyme inducers on cytochrome P450 expression in cultured human hepatocytes, Drug Metab. Dispos. 31: 421-431, 2003.
** BNF (β-naphthoflavone) was the inducer for human hepatocytes, whereas omeprazole was the inducer for Fa2N-4 cells.
*** CYP2B6 activity based on 7-ethoxy-4-trifluoromethylcoumarin O-dealkylation (4 fold) or S-mephenytoin N-demethylation (13 fold).

Example 8

Use of the Immortalized Hepatocyte Cell Lines in Toxicity Studies

Figure 22:
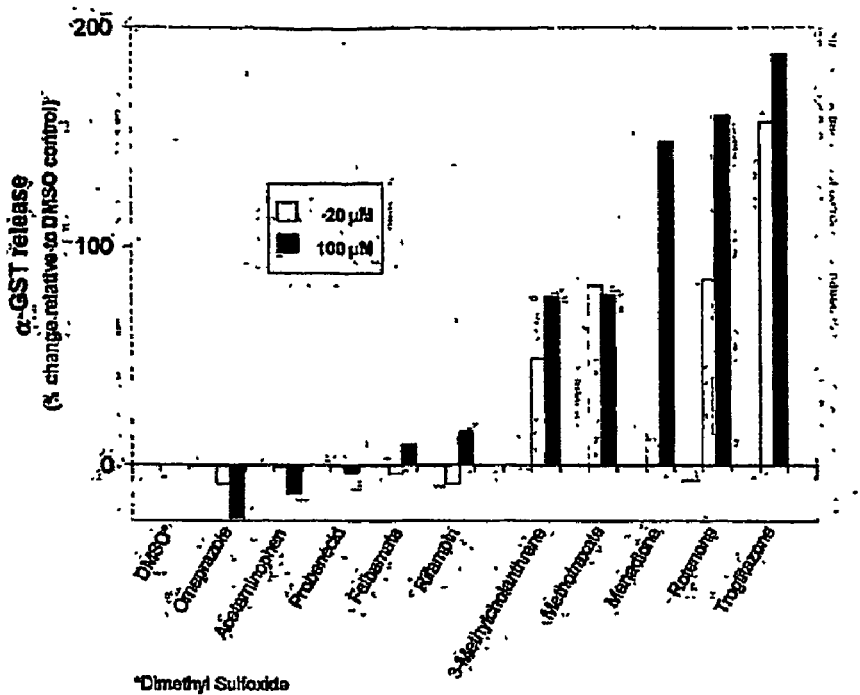
FIG. 22 shows the utility of Fa2N-4 cells in differentiating toxicants from non-toxicants by measuring the release of α-GST into media following 72-hour exposure to compounds.

Fa2N-4 and Ea1C-35 cells provide a human hepatocyte-derived system for conducting cell-based toxicity assays in vitro. FIG. 22 illustrates the use of Fa2N-4 cells in toxicity testing.

Treatment of cells with toxic concentrations (up to 100 μM) of several agents (namely 3-methylcholanthrene, methotrexate, menadione, rotenone and troglitazone) caused a loss of membrane integrity, resulting in the release into the medium of an intracellular enzyme, namely alpha-glutathione S-transferase (α-GST), which was measured with Biotrin High Sensitivity Alpha GST EIA (Biotrin International, Dublin, Ireland). In contrast, little or no α-GST was released from Fa2N-4 cells treated with non-toxic concentrations of omeprazole, acetaminophen, probenecid, felbamate or rifampin.

It should be noted that some of these agents, such as acetaminophen and felbamate, cause clinically significant liver toxicity, but only at high doses (and hence at much higher concentrations than those used in the study depicted in FIG. 22). For instance, acetaminophen toxicity is associated with doses exceeding 4 g/day as well as other concurrent environmental conditions. Exposure of the immortalized hepatocytes to the known toxicants 3-methylcholanthrene, methotrexate, menadione, rotenone, and troglitazone produced significantly greater release of α-GST from the cells.

Additional studies were conducted to compare the response of the Fa2N-4 cells with those of primary human hepatocytes, following treatment with 22 structurally diverse chemicals. Toxicity was assessed by measuring the release of lactate dehydrogenase (LDH) into the medium and a disruption of mitochondrial respiration (based on a decrease in resazurin reduction). The toxicity profiles of Fa2N-4 and primary hepatocytes were similar for most compounds, as summarized in Table 7 below. Some differences in the response of the two cell types were observed. The Fa2N-4 cells were more sensitive than primary hepatocytes to hepatotoxins such as troghtazone, hyperforin and benzo[a]pyrene, but were less sensitive to menadione.

TABLE 7

A comparison of the toxicity of 22 compounds in Fa2N-4 cells and primary human hepatocytes.

| Cellular Response | Non-toxic Compound | Toxic Compound |
|---|---|---|
| Same | Rifampin | 3-Methylcholanthrene |
| | Phenobarbital | Methotrexate |
| | Phenytoin | Rotenone |
| | Carbamazepine | Efavirenz |
| | Troleandomycin | |
| | Lansoprazole | |
| | Omeprazole | |
| | Probenicid | |
| | Felbamate | |
| | Acetaminophen | |
| | Ciglitazone | |
| | Sulfinpyrazone | |
| | Simvastatin | |
| | Fexofenadine | |
| Different | | Troglitazone * |
| | | Benzo[a]pyrene * |
| | | Hyperforin * |
| | | Menadione ** |

* Fa2N-4 cells more sensitive than human hepatocytes
** Fa2N-4 cells less sensitive than human hepatocytes Thus, these immortalized hepatocytes will be suitable for specific in vitro toxicity screens. Furthermore, the immortalized hepatocytes offer the distinct advantages of reproducibility and access.

Example 9

Induction of Drug Metabolism Enzymes (DMEs) and Multidrug Resistance 1 (MDR1) Using the Fa2N-4 Cell Line Treatment of the Fa2N-4 cells with drug was initiated 48 hours after plating. For RNA quantification, cells were exposed to drug for 48 hours. Gene expression was monitored in Fa2N-4 cells by the Invader assay (Third Wave Technologies, Madison, Wis.), a robust, yet simple, high-throughput system for quantification of mRNA transcripts. CYP1A2, CYP3A4, CYP2C9, UGT1A, and MDR1 transcripts were quantified from total RNA extracts from Fa2N-4 cells treated with a panel of known inducers and compared with vehicle controls.

Enzyme activity assays were also used to monitor the induction of CYP1 A2, CYP2C9, and CYP3A4. For enzyme activity studies, cells were exposed to drug for 72 hours. CYP3A4 activity was determined by measuring the extent of 6-beta-hydroxytestosterone formation from testosterone by mass spectrometry. CYP2C9 activity was determined by measuring the extent of 4'-hydroxydiclofenac formation. CYP1A2 activity was determined by measuring the extent of O-dealkylation of 7-ethoxyresorufin. Metabolites were quantified by comparing measurements to standard curves.

The Fa2N-4 cells responded in a similar manner as primary human hepatocytes. Treatment with 10 µM rifampin resulted in increases in CYP3A4 mRNA (17-fold) and activity (6-beta-hydroxytestosterone formation, 9-fold); and in CYP2C9 mRNA (4-fold) and activity (4'-hydroxydiclofenac formation, 2-fold). Treatment with 50 µM beta-napthoflavone resulted in increases in CYP1A2 mRNA (15-fold) and activity (7-ethoxyresorufin O-dealkylation, 27-fold). UGT1A mRNA was induced by beta-naphthoflavone (2-fold), and MDR1 (P-glycoprotein) mRNA was induced by rifampin (3-fold). Table 8 summarizes the induction data in Fa2N-4 cells for three CYPs expressed as fold-increase in mRNA compared to published data in primary hepatocytes.

TABLE 8

Summary of reported inductive response in Fa2N-4 cells as compared to response of primary human hepatocytes

| Parameter | Inducer | Fa2N-4 cells Fold-increase | Primary cells Fold-increase |
|---|---|---|---|
| CYP1A2 | B-Naphthoflavone | 1.5 | 13 |
| CYP2C9 | Rifampin | 3.8 | 3.5 |
| | Phenobarbital | 2.6 | 1.8 |
| CYP3A4 | Rifampin | 17 | 10 |
| | Phenobarbital | 9.3 | 3.3 |

Figure 23:
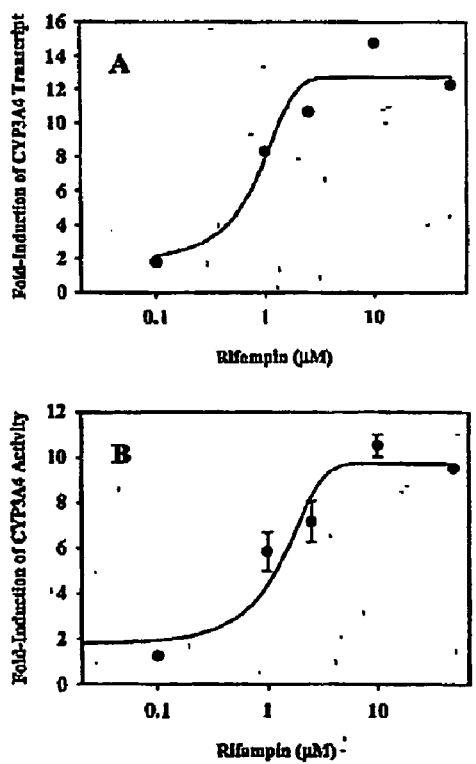
FIG. 23 shows the dose-response dependence of CYP3A4 induction by rifampin in Fa2N-4 cells. Measurement of induction of CYP3A4 was performed in Fa2N-4 cells treated with 100 nM to 50 μM rifampin. Data was fitted using SigmaPlot (version 8) using a 3-parameter sigmoidal curve. (A) Total RNA was analyzed to determine the level of CYP3A4 transcript and then compared to vehicle control to determine fold-induction. Data represents mean±SD from the data of triplicate samples. (B) CYP3A4 activity was measured by formation of the testosterone metabolite 6-beta-hydroxytestosterone and then compared to vehicle control to determine fold-induction. Data represents mean±SD from the data of triplicate samples.

In addition to examining the inductive effect of a single concentration of drug, the Fa2N-4 cells can also be used to look at dose-response relationships. For example, EC50 values were calculated based on the response of Fa2N-4 cells dosed with multiple concentrations of rifampin ranging from 100 nM to 50 µM. FIG. 23 contains EC50 plots for Fa2N-4 cells using increased CYP3A4 transcript values (FIG. 23A), as well as increased CYP3A4 enzyme activity (FIG. 23B). The calculated EC50s were 0.43 µM ($r^2$=92) and 0.77 µM ($r^2$=94), for the transcript and enzyme activity, respectively. In addition, the calculated maximum induction (Imax) values were 13-fold for the transcript endpoint and 9.7-fold for the enzyme activity endpoint.

Multiple passages of the Fa2N-4 cells have been tested for CYP3A4 induction. FIG. 24 shows response of multiple passages of Fa2N-4 cells to a CYP3A4 inducer with a weak response (50 µM dexamethasone—striped bars) and a CYP3A4 inducer that exhibits a strong response (10 µM rifampin—black bars). The open bars denote the values for cells treated with DMSO vehicle alone. Treatment with dexamethasone increased CYP3A4 transcripts, 1.6-fold and 1.5-fold at passages 21 and 36, respectively. Treatment with 10 µM rifampin increased CYP3A4 transcripts, 17-fold and 16-fold at passages 21 and 36, respectively (FIG. 24A). CYP3A4 enzyme activity was increased 2.1-fold and 2.0-fold for dexamethasone and 8.9-fold and 4.9-fold for 10 µM rifampin at passages 28 and 36, respectively (FIG. 24B).

FIG. 25 compares various multiwell formats. Regardless of the plate format, Fa2N-4 cells exhibit substantial CYP3A4 inductive response to rifampin. Fold changes in CYP3A4 transcript were 17.1-fold when using a 24-well plate, 6.6-fold when using a 48-well plate, and 5.7-fold when using a 96-well plate.

These results show that the immortalized hepatocyte cell lines of the present invention, specifically Fa2N-4 cells, can be a reliable surrogate for primary human hepatocytes, and can provide for a reliable assessment of induction of DMEs and transporters.

Example 10

Expression of Plasma Proteins By Fa2N-4 and Ea1C-35 Cell Lines

The well-differentiated nature of these cell lines is further supported by their continued secretion of adult hepatocyte function specific plasma proteins (FIG. 26). Culture medium was harvested from Fa2N-4 and Ea1C-35 cells seeded into either 60 mm plates or roller bottles and analyzed by Western blot analysis. Medium was concentrated 50× by ultrafiltration and 40 µg of total protein was loaded per lane except for albumin (10 μg total protein/lane). Blots were incubated with either monoclonal or affinity purified polyclonal antibodies against albumin, α-1-antitrypsin, Factor VIII and Factor IX and visualized using secondary antibodies conjugated to horseradish peroxidase followed by incubation with DAB substrate. As shown below in FIG. 26, both cell lines continue to express albumin, α-1-antitrypsin, and Factor IX at similar levels per ml when maintained in roller bottles as cultures maintained in plates. The expression of Factor VIII was variable and highly dependent on cell line and culture conditions. There was heterogeneity in the processing of Factor IX, an observation also seen in the human plasma-derived protein.

Both AAT and IαIp are plasma proteins that inhibit the proteolytic activity of trypsin. As shown in FIG. 26 below, immunoblot analysis clearly demonstrated the presence of AAT in the conditioned medium from both cell lines.

Taken together, all the above examples strongly indicate that the immortalized human hepatocyte cell lines of the current invention, including but not limited to the Fa2N-4 and Ea1C-35 cell lines, maintain many functional attributes characteristic of hepatocytes in vivo and are an invaluable in vitro system to produce TPPs.

Example 11

Production of Albumin.

Fa2N-4 cells were grown to confluence in T-150 flasks in serum free medium and albumin production was measured by an ELISA assay. The results of this assay are found in Table 9 below. At passages 13 and 16, the Fa2N-4 cells produced approximately 3 μg/ml of albumin. At passage 33 the Fa2N-4 cells produced approximately 9 μg/ml of albumin and at passage 41 the Fa2N-4 cells produced approximately 6 μg/ml albumin. Therefore, the immortalized hepatocyte cell lines of the present invention, specifically Fa2N-4 cells, are a potential source for the production of the TPP albumin.

TABLE 9

Concentration of albumin in FA2N-4 cells measured by ELISA assay

| Cells | Passage | Albumin in Media (μg/ml) |
|---|---|---|
| Fa2N-4 | 13 | 3.73 ± 0.64 |
| Fa2N | 16 | 3.06 ± 0.11 |
| Fa2N | 33 | 9.5 ± 0.5 |
| Fa2N | 41 | 6.17 ± 0.29 |

Example 12

Expression of Inter-Alpha-Inhibitor Proteins (IαIp).

Inter-α-inhibitor proteins (IαIp), natural serine protease inhibitors found in relatively high concentration in plasma have been shown to play roles in inflammation, wound healing and cancer metastasis. IαIp is a family of plasma proteins made and secreted by hepatocytes. The major forms of IαIp are inter-α-inhibitor (IαI, containing one light chain peptide called bikunin and two heavy chains) and pre-α-inhibitor (PαI, containing one light and one heavy chain). Recently, a monoclonal antibody that recognizes the light chain of human IαIp (MAb 69.31) was developed by scientists at Prothera Biologics (Providence, R.I.). Using MAb 69.31 in a competitive ELISA, these investigators demonstrated that plasma IαIp levels were significantly decreased in severe septic patients compared to healthy controls (Lim Y P, Bendelja K, Opal S M, Siryapom E, Hixson D C, Palardy J E. *Correlation Between Mortality and the Levels of Inter-alpha Inhibitors in Plasma of Severely Septic Patients*. Journal of Infectious Disease, 188:919-926, 2003).

Western blot analysis, using MAb 69.31 revealed that both the Fa2N-4 and Ea1C-35 cell lines continue to synthesize immunoreactive IαIp (data not shown). Subsequently, the amount of IαIp secreted into the condition medium was quantitated using an ELISA assay (see example 14 below). Thus, the Fa2N-4 and Ea1C-35 cells are a potential source for the production of the TPP IαIp.

Example 13

Production of Transferrin by Immortalized Human Hepatocytes

In order to determine if the Ea1C-35 and Fa2N-4 cells from various passages made and secreted transferrin, the cells were cultured in serum free medium without transferrin for 7 days. Conditioned culture medium was collected after 7 days and immunoblot analysis was performed using a commercially available antibody against transferrin. Human plasma was used as the positive control. Immunoblots using an antibody against transferrin revealed that the cells from all passages continue to express this plasma protein, as shown in FIG. 27. Lanes -2-5 show Ea1C-35 cells from different passages produce transferrin that is nearly identical to plasma-derived transferrin. Lanes 6-9 show Fa2N-4 cells from different passages produce transferrin that is nearly identical to plasma-derived transferrin Thus, the claimed immortalized hepatocytes, including but not limited to the Ea1C-35 and Fa2N-4 cell lines, are a potential source for the production of transferrin.

Example 14

Trypsin Inhibition Assay and Quantitation of Inter-Alpha Inhibitor Protein (IαIp) Present in Conditioned Medium The total trypsin inhibitory activity of the conditioned media includes the activity from the major serine protease inhibitors, α-1-antitrypsin and IαIp. The amount of trypsin inhibition activity secreted into the condition medium by Ea1C-35 and Fa2N-4 cells was measured using the chromogenic trypsin substrate L-BAPA (N(alpha)-Benzoyl-L-arginine-4-nitroanilide hydrochloride, Fluka Chemicals) (see Table 10). The assay is based on the ability of serine protease inhibitors to inhibit the hydrolysis of L-BAPA. Inhibition can be monitored by a decrease in the rate of delta absorbance/minute at 410 nm. The specific activity was calculated based on the biological activity per μg cellular protein. Ea1C-35 cells expressed 115 TIU/mg of protein and Fa2N-4 cells expressed 45 TIU/mg of protein.

TABLE 10

Trypsin inhibition activity and IaIp in Ea1C-35 and Fa2N-4 cells

| Cultured media | Protein Conc. after 50× ultrafiltration (UF) [mg/mL] | Trypsin Inhibition Activity after UF [TIU/mg] | IαIp conc. after UF [μg/mL] |
|---|---|---|---|
| Ea1C-35 | 4.50 | 115.0 | 20.08 |
| Fa2N-4 | 9.02 | 45.10 | 4.03 |

The amount of IαIp in the media was measured by a competitive ELISA using MAb 69.31 (e.g. a polyclonal antibody specific against human IαIp). The ELISA was performed as follows: 96 well Immunolon-4 plates (Dynex, USA) were coated with purified IαIp (300 ng) in 50 mM carbonate buffer pH 9.6 and incubated overnight at 4° C. A serial dilution of purified human plasma derived IαIp. in PBS containing 1% rat serum was used to establish a standard curve. For the quantitative analysis of IαIp levels in culture media, 50 μL of media or serially diluted IαIp were added to individual wells of a 96 well plate. After the addition of 50 μL of MAb 69.31 to each well, plates were incubated for 1 hr at 37° C. and subsequently washed using an automated plate washer (Labsystem). The bound MAb 69.31 was detected by adding HRP-conjugated goat anti-mouse IgG (human absorbed) (Biosource, Camarillo, Calif., USA) for 1 hr at 37° C. After washing, 100 μL 1-Step ABTS (Pierce, Rockford, Ill., USA) was added to the wells and the absorbance at 405 nm was measured on ELISA plate reader (BioTek). Each sample was tested in triplicate. Unconditioned culture media was used as baseline control. The results are summarized in Table 10. Ea1C-35 cells expressed 20 μg/ml of IαIp and Fa2N-4 cells expressed 4 μg/ml of IαIp.

These results demonstrate that the immortalized hepatocytes of this invention are a good potential source for the production of TPPs, such as AAT and IαIp.

Example 15

Two-Dimensional Gel Analysis

2-D gel electrophoretic analysis was used to separate the secreted proteins of the Fa2N-4 and Ea1C35 cell lines. Using Invitrogen's ZOOM IPGRunner system, the first IEF separation of the proteins was carried out using fixed pH gradient strip (pH range of 3-10) followed by the second dimension separation using 4-12% Tris-Gycine SDS-PAGE. In both cell lines multiple spots of proteins could be identified as possible candidates for TPPs. (FIG. 28A. Fa2N-4; 28B, Ea1C35). After the 2-dimensional gel separation the secreted proteins of the Ea1C35 cell line were transferred onto nitrocellulose and Western blot analysis using anti-Factor IX antibody was performed. Reactive protein with MW of 70 KD and pI 6.5-7.0 was detected (FIG. 28C). Thus, the claimed immortalized hepatocyte cell lines of the present invention are a potential source of TPPs, such as Factor IX.

Example 16

Cell Line Expansion and Quantitation of Plasma Protein Secretion

The economical production of TPPs using cultured immortalized human hepatocytes as producer cells can only be accomplished if the cells continue to make and secrete these TPPs when expanded in mass culture. In order to initially evaluate this question, Fa2N-4 cells were grown to confluence in T25, T75 and T150 culture flasks and selected plasma proteins were quantitated using ELISA assays in combination with capture antibodies that recognized albumin, AAT or IαIp. An equivalent number of cells were initially plated per square cm, 5, 15 and 30 million cells, respectively. Conditioned medium was collected for 3 days, pooled, concentrated 10× by ultrafiltration and assayed. As shown in FIG. 29 below, the total expression of each plasma protein was approximately proportional to cell number. Values represent the mean±SD for triplicate samples. Over the 3-day period cells cultured in T150 flasks produced approximately 200 μg albumin, 500 ng IαIp and 150 ng AAT. This shows that the immortalized hepatocyte cell lines claimed in the present invention are a potential source for the production of TPPs.

Example 17

Effect of Culture Period on Albumin Secretion

Figure 30:
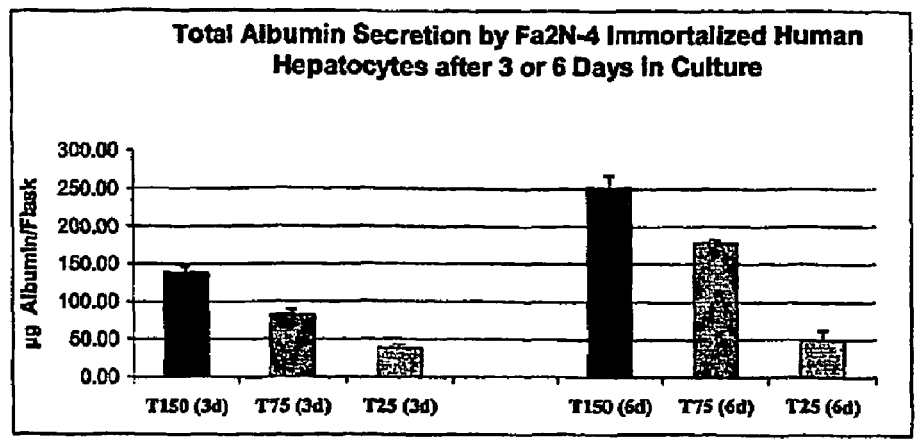
FIG. 30 shows total albumin secretion by Fa2N-4 cells after three and six days in culture in T25, T75, and T150 flasks.

We plan to use immortalized human hepatocytes as biofactories for the commercial production of TPPs. Therefore, it is essential that TPP secretion must not be significantly decreased in long-term culture. We recently initiated a study in order to evaluate this question, Fa2N-4 cells were grown in T25, T75 and T150 culture flasks, as described above in the previous examples, and albumin production was measured as an indicator of overall protein secretion. Conditioned medium was collected on Day 3; cells were re-fed and resampled on Day 6. Albumin secretion was analyzed by an ELISA assay. The results indicate that albumin secretion continues to increase over the 6 day collection period irrespective of the plating format (see FIG. 30). Of particular note, there is a dramatic increase in albumin when cells were cultured in the T75 and T150 flasks. Since total cellular protein does not significantly increase with time in culture (data not shown), it seems likely that these results are due to enhanced production as a result of adaptation to culture conditions and not the result of a dramatic increase in cell number per flask.

Example 18

Effect of Tumor Necrosis Factor α (TNFα) on Plasma Protein Secretion

Production of some plasma proteins can be modulated by acute phase proteins, such as TNFα in vivo. The effect of treatment with TNFα on the secretion of AAT was studied. Fa2N-4 cells were maintained in serum free proprietary MFE medium containing TNFα (0, 1, 5, or 10 ng/ml) for 3 days. As shown in Table 11 below, the secretion of ATT was most notably increased by the inclusion of 5 ng/ml TNFα in the serum free culture medium. Values are the average of duplicate samples. Thus, it may be possible to increase ATT production using this cytokine. Therefore, treatment of the immortalized hepatocyte cell lines of the present invention with TNFα may be an effective way to increase the production of TPPs.

TABLE 11

Effect of TNFα on TPP expression

| Sample | Concentration of Tumor Necrosis Factor Alpha | Antitrypsin (ng)/μg Protein | Antitrypsin (ng)/well |
|---|---|---|---|
| #1 | TNF 0 ng/ml | 0.21 | 14.00 |
| #2 | TNF 1 ng/ml | 0.34 | 21.00 |
| #3 | TNF 5 ng/ml | 0.43 | 44.73 |
| #4 | TNF 10 ng/ml | 0.48 | 32.93 |

Example 19

Effect of Dexamethasone on Expression of Plasma Proteins by Immortalized Human Hepatocytes Albumin expression is regulated in part by a dexamethasone inducible promoter (Nakmura, et al, J Biol Chem, 261: 16883-16888, 1986). In order to examine the effects of dexamethasone on the production and secretion of albumin by immortalized human hepatocytes, Fa2N-4 cells (passage 32) were cultured on type I collagen dishes with or without dexamethasone in the culture medium for 48 hrs and albumin expression was measured by an ELISA assay. Values represent the average of duplicate samples. As summarized in Table 12 below the secretion of albumin was significantly decreased in the absence of dexamethasone.

Therefore, treatment with dexamethasone may be an effective way to increase the production of TPPs in the claimed immortalized hepatocyte cell lines of this present invention.

TABLE 12

Effect of dexamethasone on TPP expression

| Concentration of Dexamethasone | Albumin (µg/ml) |
|---|---|
| 0 | 40.0 |
| 1.0 µM | 100.0 |

Example 20

Ability to Produce and Express Therapeutic Plasma Proteins (TPPs)

The ability of our Fa2N-4 cell line to correctly produce an immunologically reactive TPP was illustrated with the production of immuno-reactive human growth hormone (hGH).

Conditioned media was withdrawn from each well after 24 and/or 48 hours and was subsequently used for an ELISA-based immunodetection assay. The ELISA assay is a colorimetric enzyme immunoassay for the quantitative determination of secreted hGH utilizing the sandwich ELISA principle. Microtiter plate pre-bound antibodies to hGH bind to secreted hGH contained in the conditioned media. Subsequently, a digoxigenin labeled hGH antibody binds to a second epitope of the hGH peptide contained in the conditioned media and retained on the microtiter plate. An antibody to digoxigenin, which is conjugated to peroxidase is then added and followed by the peroxidase substrate ABTS. The peroxidase-catalyzed cleavage of the substrate yields a colored reaction product that can be easily detected using a microtiter plate reader.

Figure 31:
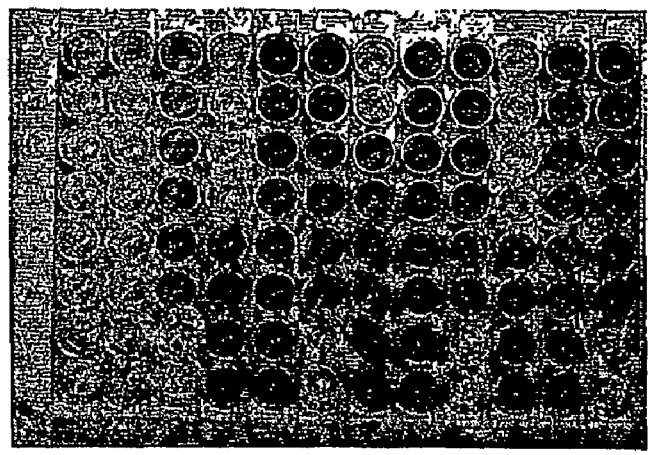
FIG. 31 shows a photograph of the ELISA plate 1 containing a colorimetric enzyme immunoassay for the quantitative determination of secreted hGH utilizing the sandwich ELISA principle. The key for this plate is shown below in Table 13.
Figure 32:
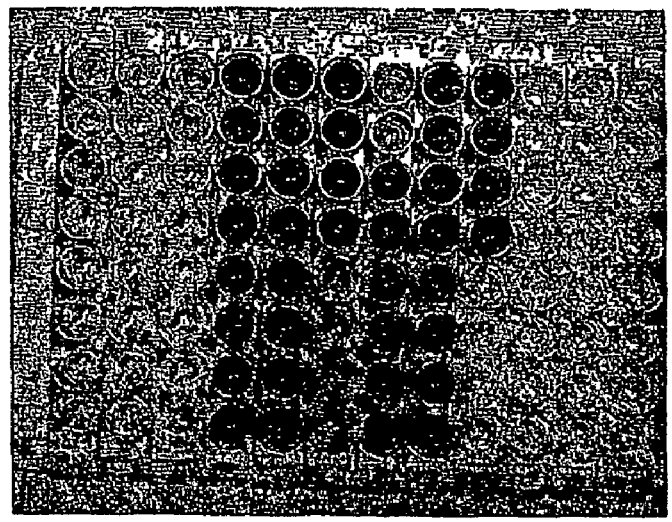
FIG. 32 shows a photograph of the ELISA plate 2 containing a colorimetric enzyme immunoassay for the quantitative determination of secreted hGH utilizing the sandwich ELISA principle. The key for this plate is shown below in Table 13.

Our results confirm that using either transfection kit and harvesting the conditioned media at either 24 or 48 hours post-transfection, the Fa2N-4 cells produce extraordinarily large quantities of double immunodetected hGH while transfection with LacZ or no plasmid negative controls produced no detectable levels of hGH. A photograph of the ELISA plates 1 and 2 are shown in FIG. 31 and FIG. 32, respectively. The key for FIGS. 31 and 32 is shown below in Table 13.

TABLE 18

Legend for ELISA plates shown in FIGS. 31 and 32

| | 1 | 2 | 3 | 4 | 5 | 6 | 7 | 8 | 9 | 10 | 11 | 12 |
|---|---|---|---|---|---|---|---|---|---|---|---|---|
| Plate 1 | | | | | | | | | | | | |
| A | Blank | Std 0 | Std 80 | 1QLacZ 2 | 1Q(1:10)3 | 1Q(1:30)1 | 1Neg2' | 1Q(1:10)3' | 1Q(1:30)1' | 2QLacZ 2 | 2Q(1:10)3 | 2Q(1:30)1 |
| B | Blank | Std 0 | Std 80 | 1QLacZ 2 | 1Q(1:10)3 | 1Q(1:30)1 | 1Neg2' | 1Q(1:10)3' | 1Q(1:30)1' | 2QLacZ 2 | 2Q(1:10)3 | 2Q(1:30)1 |
| C | Blank | Std 10 | Std 160 | 1QLacZ 3 | 1Q(1:20)1 | 1Q(1:30)2 | 1Neg3' | 1Q(1:20)1' | 1Q(1:30)2' | 2QLacZ 3 | 2Q(1:20)1 | 2Q(1:30)2 |
| D | Blank | Std 10 | Std 160 | 1QLacZ 3 | 1Q(1:20)1 | 1Q(1:30)2 | 1Neg3' | 1Q(1:20)1' | 1Q(1:30)2' | 2QLacZ 3 | 2Q(1:20)1 | 2Q(1:30)2 |
| E | Blank | Std 20 | Std 320 | 1Q(1:10)1 | 1Q(1:20)2 | 1Q(1:30)3 | 1Q(1:10)1' | 1Q(1:20)2' | 1Q(1:30)2' | 2Q(1:10)1 | 2Q(1:20)2 | 2Q(1:30)3 |
| F | Blank | Std 20 | Std 320 | 1Q(1:10)1 | 1Q(1:20)2 | 1Q(1:30)3 | 1Q(1:10)1' | 1Q(1:20)2' | 1Q(1:30)3' | 2Q(1:10)1 | 2Q(1:20)2 | 2Q(1:30)3 |
| G | Blank | Std 40 | 1QLacZ 1 | 1Q(1:10)2 | 1Q(1:20)3 | 1Neg1' | 1Q(1:10)2' | 1Q(1:20)3' | 2QLacZ 1 | 2Q(1:10)2 | 2Q(1:20)3 | 2Neg1' |
| H | Blank | Std 40 | 1QLacZ 1 | 1Q(1:10)2 | 1Q(1:20)3 | 1Neg1' | 1Q(1:10)2' | 1Q(1:20)3' | 2QLacZ 1 | 2Q(1:10)2 | 2Q(1:20)3 | 2Neg1' |
| Plate 2 | | | | | | | | | | | | |
| A | Blank | | | 2Neg3' | 2Q(1:20)1' | 2Q(1:30)2' | ILacZ 3 | I(1.0)1 | I(2.0)2 | | | Blank' |
| B | Blank | | | 2Neg3' | 2Q(1:20)1' | 2Q(1:30)2' | ILacZ 3 | I(1.0)1 | I(2.0)2 | | | Blank' |
| C | Blank | | | 2Q(1:10)1' | 2Q(1:20)2' | 2Q(1:30)3' | I(0.5)1 | I(1.0)2 | I(2.0)3 | | | Blank' |
| D | Blank | | | 2Q(1:10)1' | 2Q(1:20)2' | 2Q(1:30)3' | I(0.5)1 | I(1.0)2 | I(2.0)3 | | | Blank' |
| E | Blank | | | 2Q(1:10)2' | 2Q(1:20)3' | ILacZ 1 | I(0.5)2 | I(1.0)3 | | | | Blank' |
| F | Blank | | | 2Q(1:10)2' | 2Q(1:20)3' | ILacZ 1 | I(0.5)2 | I(1.0)3 | | | | Blank' |
| G | Blank | 2Neg2' | | 2Q(1:10)3' | 2Q(1:30)1' | ILacZ 2 | I(0.5)3 | I(2.0)1 | | | | Blank' |
| H | Blank | 2Neg2' | | 2Q(1:10)3' | 2Q(1:30)1' | ILacZ 2 | I(0.5)3 | I(2.0)1 | | | | Blank' |

Key—
Blank = Substrate
Std X = Standard of X ng/ml hGH
XQLacZ Y = Sample Y obtained X days after transfection of a LacZ control plasmid into 0.5 × 10(6) cells using the Qiagen kit
XQ(1:Y)Z = Sample Z obtained X days after transfection of a 1:Y ratio of DNA:Effectene reagent into 0.5 × 10(6) cells using the Qiagen kit
XNegY' = Sample Y obtained X days after transfection of no DNA into 0.8 × 10(6) cells using the Qiagen kit
XQ(1:Y)Z' = Sample Z obtained X days after transfection of a 1:Y ratio of DNA:Effectene reagent into 0.8 × 10(6) cells using the Qiagen kit
ILacZ X = Sample X obtained one day after transfection of a LacZ control plasmid into 0.7 × 10(6) cells using the Invitrogen kit
I(X)Y = Sample Y obtained one day after transfection of X ug DNA into 0.7 × 10(6) cells using the Invitrogen kit
Blank' = Buffer On the day prior to transient transfection, Fa2N-4 cells were plated at a density of 0.5-0.8×10$^6$ cells per well in six-well Nunc plates using 10% NBCS-MFE medium. On the day of transfection the cells were washed one time to remove serum and a CMV-based plasmid, containing the complete cDNA for hGH, was transiently transfected into the Fa2N-4 cells using either an Invitrogen Lipofectamine Plus or a Qiagen Effectene transfection reagent kit. The transfections were performed as per the manufacturers' protocols.

Example 21

Immunophehenotypic Characterization of the EA1C-35 and Fa2N-4 Cell Lines

Both the Ea1C-35 (passage 26) and Fa2N-4 (passage 30) cell lines were phenotyped by indirect immunofluorescence analysis using a panel of antibodies against different hepatocyte or bile duct markers as well as against the SV40 immortalizing gene. The results from this analysis are summarized in the Table 14 below:

TABLE 14

Expression of various hepatocyte and bile duct markers and the SV40 immortalizing gene in Ea1C-35 and Fa2N-4 cells

| Marker | Ea1C-35 (% positive Cells) | Fa2N-4 (% positive Cells) |
|---|---|---|
| Albumin | 90 | 100 |
| Alpha Fetoprotein | 0 | 0 |
| Connexin 32 | 50 | 80 |
| CD 81 | 100 | 100 |
| CD49f (integrin alpha 6 chain) | 0 | 0 |
| SV40 T-antigen | 100 | 100 |

The expression of connexin 32 was density dependent. When cells grew to confluent monolayers, a subpopulation of Ea1C-35 and Fa2N-4 cells express this gap junctional protein that is only expressed by hepatocytes in adult liver tissue.

Figure 33:
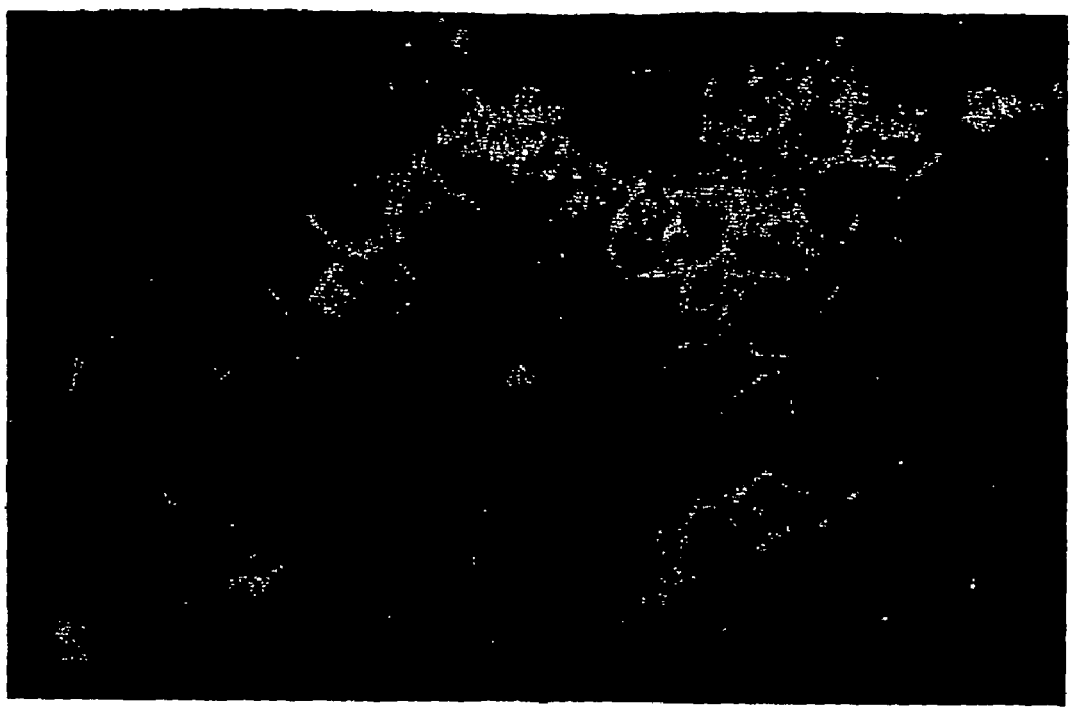
FIG. 33 shows a photomicrograph of Fa2N-4 cells immunstained for CD81. Note that expression of CD81 is localized to the plasma membrane.

All cells expressed SV40 T-antigen, the immortalizing gene. Expression of immunodetectable SV40 T-antigen was localized specifically to the nucleus. The well-differentiated nature of the immortalized liver cells is indicated by the strong expression of the adult hepatocyte specific lineage markers, albumin and connexin 32 and the lack of the fetal hepatocyte marker, alpha fetoprotein. The cells do not express CD49f, a bile duct marker. The cells express CD81, the putative receptor for hepatitis C virus glycoprotein-mediated viral infection. A photomicrograph of Fa2N-4 cells immunostained for CD81 is shown in FIG. 33. Note that expression of CD81 is localized to the plasma membrane.

Other Embodiments

All references discussed above are herein incorporated by reference in their entirety for all purposes. While this invention has been particularly shown and described with references to preferred embodiments thereof, it will be understood by those skilled in the art that various changes in form and details may be made therein without departing from the spirit and scope of the invention as defined by the appended claims.

We claim:

1. A virally-immortalized hepatocyte, said hepatocyte;
   (a) being derived from a normal liver cell;
   (b) being nontumorigenic;
   (c) naturally producing endogenous therapeutic plasma proteins (TPPs); and
   (d) being stable in culture and not undergoing dedifferentiation in culture, wherein said hepatocyte is Fa2N-4 (ATCC #PTA-5566).

2. A virally-immortalized hepatocyte, said hepatocyte;
   (a) being derived from a normal liver cell;
   (b) being nontumorigenic;
   (c) naturally producing endogenous therapeutic plasma proteins (TPPs); and
   (d) being stable in culture and not undergoing dedifferentiation in culture, wherein said hepatocyte is EalC-35 (ATCC #PTA-5565).

* * * * *